US009522001B2

(12) United States Patent
Bui et al.

(10) Patent No.: US 9,522,001 B2
(45) Date of Patent: Dec. 20, 2016

(54) SURGICAL APPLIANCE KIT AND SYSTEM FOR RELEASABLY SECURING A SURGICAL APPLIANCE TO A SURGICAL FIELD AND METHOD OF ASSEMBLING THE SURGICAL APPLICANCE KIT

(75) Inventors: Phong Duy Bui, San Diego, CA (US); Ruel Flores Salvador, San Diego, CA (US)

(73) Assignee: Operating Room Innovations, Inc., Coronado, CA (US)

( * ) Notice: Subject to any disclaimer, the term of this patent is extended or adjusted under 35 U.S.C. 154(b) by 995 days.

(21) Appl. No.: 13/445,808

(22) Filed: Apr. 12, 2012

(65) Prior Publication Data

US 2013/0269713 A1    Oct. 17, 2013

(51) Int. Cl.
*A61B 19/08* (2006.01)
*A61B 17/06* (2006.01)
(Continued)

(52) U.S. Cl.
CPC ......... *A61B 17/06114* (2013.01); *A61B 46/23* (2016.02); *A61B 50/33* (2016.02);
(Continued)

(58) Field of Classification Search
CPC . A61B 1/00059; A61B 1/00144; A61B 17/00; A61B 19/00; A61B 19/02; A61B 19/026; A61B 19/027; A61B 19/021; A61B 19/08; A61B 19/088; A61B 19/10; A61B 19/103; A61B 19/10619; A61B 19/44
(Continued)

(56) References Cited

U.S. PATENT DOCUMENTS 3,346,464 A * 10/1967 Ernst ............................... 435/31
3,654,047 A     4/1972 Berkowitz
(Continued)

FOREIGN PATENT DOCUMENTS

DE   WO 2012007089 A1 *  1/2012   ......... B60R 13/0206
JP       2004097533          1/2004

OTHER PUBLICATIONS

Servicemed, Ltd., 2010. Accessories for Surgical Drapes [online] Servicemed, Ltd., available from: http://servicemed.eu/index.php?option=com_content&view=article&id=85%3Aaccessories-for-surgical-drapes&catid=38%3A3m-surgery&Itemid=94&lang=en [Accessed Dec. 27, 2012].
(Continued)

*Primary Examiner* — Ophelia A Hawthorne
(74) *Attorney, Agent, or Firm* — Jerry F. Putts; James R. McDaniel

(57) ABSTRACT

Surgical appliance kit and system for releasably securing a surgical appliance to a surgical field and method of assembling the surgical appliance kit. The surgical appliance kit and system includes a surgical tray having the surgical appliance and a plurality of hook-and-loop attachment members disposed thereon. A cover is attached to the surgical tray and covers the surgical appliance and the plurality of attachment members. In use, a "hook" attachment member is adhesively attached to the surgical appliance and a "loop" attachment member is adhesively attached to the surgical field. The hook attachment member is placed into engagement with the loop attachment member. In this manner, the surgical appliance is releasably secured to the surgical field, so that the surgical appliance will not inadvertently fall from the surgical field.

38 Claims, 17 Drawing Sheets

(51) Int. Cl.

| | |
|---|---|
| A61B 17/02 | (2006.01) |
| A61B 17/068 | (2006.01) |
| A61B 10/06 | (2006.01) |
| A61M 25/02 | (2006.01) |
| A61B 18/14 | (2006.01) |

(52) U.S. Cl.
CPC .............. *A61B 10/06* (2013.01); *A61B 17/02* (2013.01); *A61B 17/0218* (2013.01); *A61B 18/14* (2013.01); *A61B 2017/0688* (2013.01); *A61B 2017/06142* (2013.01); *A61B 2046/201* (2016.02); *A61B 2046/234* (2016.02); *A61B 2050/0065* (2016.02); *A61B 2050/314* (2016.02); *A61M 2025/026* (2013.01); *A61M 2025/0266* (2013.01)

(58) Field of Classification Search
USPC ........ 128/846, 849, 852; 206/339, 363, 364, 206/438, 557, 656, 776; 220/662
See application file for complete search history.

(56) References Cited

U.S. PATENT DOCUMENTS

| | | | | |
|---|---|---|---|---|
| 4,121,714 | A * | 10/1978 | Daly et al. ..................... | 206/363 |
| 4,482,053 | A * | 11/1984 | Alpern et al. ................. | 206/439 |
| 4,523,679 | A * | 6/1985 | Paikoff et al. ................. | 206/370 |
| 4,570,682 | A * | 2/1986 | Bachmann ..................... | 139/1 C |
| 4,944,311 | A | 7/1990 | Eldridge, Jr. et al. | |
| 4,976,700 | A | 12/1990 | Tollini | |
| 5,010,899 | A | 4/1991 | Thompson | |
| 5,082,111 | A | 1/1992 | Corbitt et al. | |
| 5,098,399 | A | 3/1992 | Tollini | |
| 5,147,322 | A | 9/1992 | Bowen et al. | |
| 5,284,244 | A | 2/1994 | O'Toole et al. | |
| 5,304,146 | A | 4/1994 | Johnson et al. | |
| 5,315,985 | A | 5/1994 | Decarie et al. | |
| 5,344,017 | A * | 9/1994 | Wittrock .................... | 206/459.1 |
| 5,439,648 | A * | 8/1995 | Balderson et al. ............. | 422/86 |
| 5,624,403 | A * | 4/1997 | Jaquith ......................... | 604/179 |
| 5,699,909 | A | 12/1997 | Foster | |
| 6,055,987 | A | 5/2000 | Griesbach | |
| 6,073,767 | A * | 6/2000 | Cohen et al. ................. | 206/363 |
| 6,767,509 | B1 * | 7/2004 | Griesbach et al. ............. | 422/29 |
| 6,769,546 | B2 * | 8/2004 | Busch .......................... | 206/571 |
| 6,889,839 | B1 * | 5/2005 | Rosten et al. ................ | 206/583 |
| 7,096,870 | B2 | 8/2006 | Lamprich | |
| 7,401,703 | B2 * | 7/2008 | McMichael et al. ......... | 206/570 |
| 7,621,009 | B2 * | 11/2009 | Elhabashy ...................... | 5/622 |
| 7,770,583 | B2 | 8/2010 | Harris et al. | |
| 7,922,983 | B2 * | 4/2011 | Prokash et al. ............... | 422/294 |
| 8,365,910 | B2 * | 2/2013 | Valaie et al. .................. | 206/363 |
| 8,631,935 | B2 * | 1/2014 | Tomes et al. ................. | 206/370 |
| 2006/0061696 | A1 | 3/2006 | Miyazawa | |
| 2006/0260967 | A1 * | 11/2006 | Clarke et al. ................. | 206/438 |
| 2007/0235038 | A1 * | 10/2007 | Alinsod et al. ............... | 128/849 |
| 2013/0104909 | A1 * | 5/2013 | Barrier et al. ................ | 128/852 |

OTHER PUBLICATIONS

Speedtech International, Inc., 2011, Pressure Sensitive/Sticky Back Tape [online] Speedtech International, Inc., available from: http://www.speedtechinternational.com/Comparing-SPEEDWRAP-VEL-CRO-brand-Ties,aspx> [Accessed Dec. 27, 2011].
Administrator, Surgical Instrumentation, SPD Level I Training Manual—Section VI.PDF, 2001.
Storm2K.com, available from: < http://www.storm2k.com/surgicalinstrumentation.pdf> [Accessed Dec. 27, 2011].
DeRoyal, Inc., 2011, Surgical Selection, Solutions & Value [online] DeRoyal, Inc., availabie from < http://www.deroyal.com/FileDisplay.aspx?id=107> [Accessed Dec. 27, 2012].
gplus.com, 2011. Is There a Demand for Surgical Version of the Post-It Note? [Online] GPlus.com, available from: https://www.gplus.com/Healthcare/Discussion/Is-there-a-demand-for-surgical-version-of-the-post-it-note#remark-7949 [Accessed Dec. 27, 2011].
ISIPS International Sharps Injury Prevention Society, 2011. Surgical Sharps Protection [online] ISIPS International Sharps Injury Prevention Society, available from: < http://www.isips.org/Surgical_Sharps_Protection.php> [Accessed Dec. 27, 2011].
Administrator, Surgical Instrumentation, SPD Level I Training Manual—Section VI.PDF, 2001. [Online] Storm2K.com, available from: < http://www.storm2k.com/surgicalinstrumentation.pdf> [Accessed Dec. 27, 2011].
DeRoyal, Inc., 2011. Surgical Selection, Solutions & Value [online] DeRoyal, Inc., available from < http://www.deroyal.com/FileDisplay.aspx?id=107> [Accessed Dec. 27, 2011].
Velcro Industries B.V., 2010. Velcro® brand Adhesives—Pressure Sensitive, Fire Retardant, Solvent and Heat Activated [online] Amsterdam, The Netherlands, Velcro Industries B.V., available from < http://www.velcro.com/uploads/pdf/B_Adhesive_Guide.pdf> [Accessed Dec. 27, 2011].

* cited by examiner

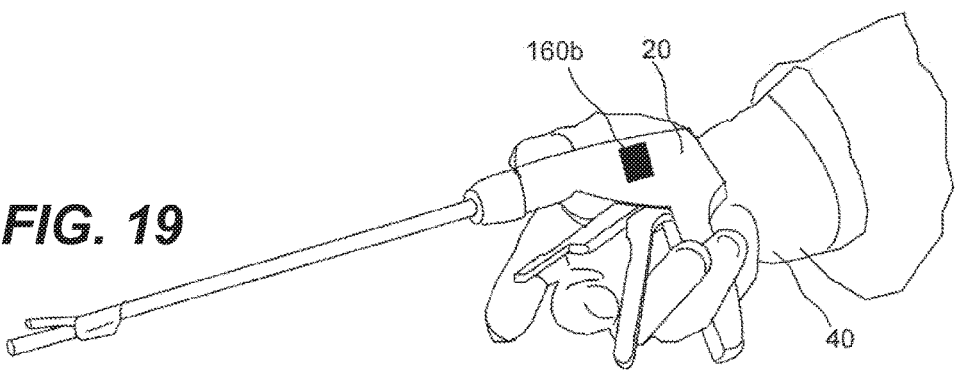
FIG. 19
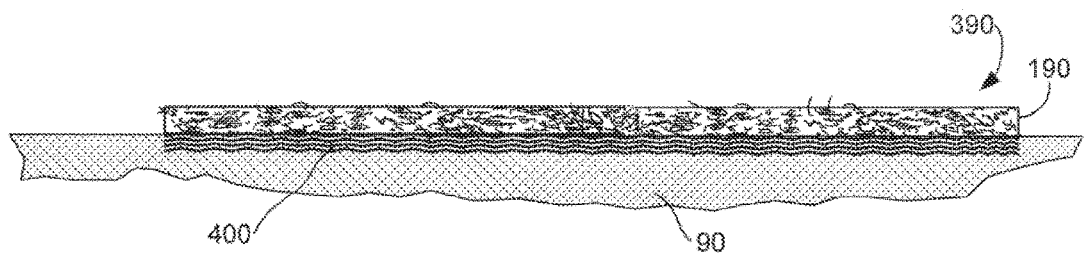

SURGICAL APPLIANCE KIT AND SYSTEM FOR RELEASABLY SECURING A SURGICAL APPLIANCE TO A SURGICAL FIELD AND METHOD OF ASSEMBLING THE SURGICAL APPLICANCE KIT

FIELD OF THE INVENTION

This invention generally relates to surgical apparatus and methods and more particularly relates to a surgical appliance kit and system for releasably securing a surgical appliance to a surgical field and a method of assembling the surgical appliance kit.

BACKGROUND OF THE INVENTION

During surgery, a surgical drape is laid over a patient so as to cover a portion of the patient at or near a surgical field. A "surgical field", which is also commonly referred to as a "surgical site", is an operating field that is an isolated area where an invasive procedure or surgery is performed and that must be kept sterile by aseptic techniques. Surgical drapes are sterilized linens placed on the patient and around the surgical field in a manner that delineate sterile areas. Surgical appliances are placed on the surgical drape, such that the surgical appliances are within easy reach of the surgeon or the surgeon's assistant during surgery.

The surgical appliances used during surgery are typically scalpels for making incisions, retractors for holding open a portion of the body, forceps for holding organs and tissue, scissors for suturing and cutting, needle holders for holding needles while suturing tissue, tubing for allowing drainage or administration of fluids, staplers for closing the incisions, electrocautery devices for removing unwanted tissue or for sealing blood vessels, and other surgical appliances.

It is important that surgical appliances are contamination-free to reduce risk of patient infection. Contaminants (i.e., bioburden) that can cause infections include pathogens and microbial organisms, such as *clostridia, streptococci, staphylococci, E. coli bacilli* and other pathogens, bacterium and microbial organisms. Exogenous sources for these surgical field infectious pathogens, bacterium and microbial organisms include surgical personnel, the operating room environment, surgical instruments, and various materials brought to the surgical field. Such pathogens, bacterium and microbial organisms acquired by a patient while in the operating room can lead to serious post-operative, nosocomial (i.e., hospital-acquired) health complications, such as hepatitis, bronchitis, sepsis from intravenous sites, and even death. In the United States, approximately 780,000 of 30 million surgical procedures result in nosocomial surgical field infections. It has been estimated that nosocomial infections result in between 17,000 and 70,000 deaths annually in the United States.

Nosocomial patient infections may also result in medical malpractice tort liability for hospital personnel and/or the hospital facility, if medical personnel or the hospital fails to provide hygienic treatment and the infection is allowed to spread and cause further injury. In a 2005 study, it was estimated that the cost of jury awards for all medical malpractice cases in the United States was about 3.6 billion dollars. In 2006, the median medical malpractice award in the United States was $175,000.

In order to reduce risk of nosocomial patient infection during surgery, surgical appliances are routinely pre-sterilized. Especially in the case of re-usable surgical appliances, the surgical appliance is pre-soaked in a chemisteriliant solution and then hand scrubbed or subjected to ultrasonic cleaning. Pre-soaking, scrubbing and ultrasonic cleaning are performed so that any debris present on the surgical appliance cannot prevent direct contact between a sterilizing agent and microorganisms residing on the surgical appliance. In addition to pre-soaking, scrubbing and ultrasonic cleaning, pre-sterilization techniques also include chemical treatment, subjection to ionizing radiation, placement in a sterilizing chemical vapor or gas, and/or exposure to heat, as well as other pre-sterilization techniques. More specifically, chemical treatment may include use of chemicals with biocide capability, such as isopropyl alcohol, formaldehyde, bleach, tincture iodine, mercurochrome and other chemicals. Also, surgical appliances, especially surgical appliances having polymer components that cannot withstand elevated temperatures, can be exposed to a Cobalt-60 radiation source. The Cobalt-60 radiation source emits high-energy gamma ionizing radiation to kill microbial organisms. The radiation source can also be an electrical device that generates electron radiation in the form of an electron beam for killing microbial organisms. The chemical vapor or gas, which may be ethylene oxide gas, may also be used as a sterilizing agent. In the case of heat application, the surgical appliance is placed in an autoclave and subjected to moist heat in the form of pressurized steam or placed in an oven and subjected to dry heat. Dry heat may be applied at a predetermined elevated temperature, such as 320° F. (i.e., 160° C.), for a predetermined time duration, such as 60 minutes or wet heat may be applied at the same temperature of 320° F. (i.e., 160° C.), for a predetermined time duration, such as less than one minute. Use of the pre-sterilization techniques mentioned hereinabove reduces risk of patient infection when surgical appliances are delivered to and placed in the surgical field on the surgical drape.

However, a surgical appliance can sometimes slip and fall from the surgical drape and land on the operating room floor. If this occurs, the pre-sterilized surgical appliance may become contaminated with infectious microbial organisms and may even break. In order to reduce the risk of patient infection and possible medical malpractice tort liability, the surgical appliance used during the surgical procedure must be replaced. In this case, the surgical procedure is interrupted, thereby causing more time to complete the surgical procedure. If sterilization of the surgical appliance is routinely performed inside the operating room, hospital personnel must repeat the previously mentioned sterilization procedures for the replacement surgical appliance. If the sterilized surgical appliance was delivered to the operating room contained in a package, another package containing a sterilized appliance must be obtained. Thus, re-sterilizing replacement surgical appliances in the operating room or obtaining another package containing a sterilized surgical appliance results in additional time to complete the surgical procedure, particularly if a sterile replacement surgical appliance is not immediately available. In addition, interruption of the surgical procedure can even pose a health risk to the patient. The health risk to the patient may arise because the surgeon will divert his eyes and attention away from the exacting surgery being performed in order to attend to replacing the surgical appliance. Therefore, it is important that surgical appliances are prevented from slipping from the surgical drape and falling to the operating room floor.

Various approaches have been attempted to address the issues mentioned hereinabove. For example, U.S. Pat. No. 4,944,311 titled "Surgical Instrument Retainer" and issued Jul. 31, 1990 in the names of Eldridge, Jr. et al. discloses a reusable, flexible surgical drape which is laid over a patient adjacent the surgical field and which retains surgical instruments thereon to facilitate access to the instruments. A plurality of magnets is embedded in the drape so as to retain magnetizable instruments placed on the drape by means of magnetic force. A non-megnetized portion is provided in the center of the drape for storage of non-magnetizable instruments. However, according to this patent, it appears that the non-magnetizable instruments are merely placed in the center of the drape rather than being securely attached to the center of the drape. Therefore, it appears possible that the non-magnetizable instruments can be inadvertently knocked or displaced from the center of the drape and fall to the operating room floor during the surgical procedure. Also, this patent appears directed to a surgical drape upon which surgical instruments are placed to facilitate access to the instruments and does not appear specifically directed to a surgical drape for preventing instruments from falling to the floor of the operating room.

Another approach is disclosed in U.S. Pat. No. 4,976,700 titled "Surgical Securing Tape" and issued Dec. 11, 1990 in the name of Dennis R. Tollini. The Tollini patent discloses a securing tape for securing to a patient's skin or to a support, a medical device such as tubing, a catheter, an intravenous needle, or the like. According to this patent, the securing tape includes an elongated tape having base portions and a central tab formed integrally therewith, The securing tape also includes pressure-sensitive tape on the base portions and on an exposed window of the tab. The securing tape further includes hook and pile fastener portions on opposite sides of the exposed adhesive on the tab and on the base portion facing the tape's exposed adhesive. However, it appears the Tollini patent is directed to securing tubes, catheters, intravenous needles, or the like and is not directed to securing larger surgical instruments of non-tubular shape, such as scalpels, retractors, forceps, scissors, staplers, and other larger, non-tubular instruments, Yet another approach is disclosed in U.S. Pat. No. 5,315,985 titled "Endoscopic Instrumentation Kit And Package Therefor" and issued Mar. 21, 1994 in the names of Andre P. Decarie, et al. This patent discloses an endoscopic or laparoscopic instrumentation kit including at least one obturator and at least two sleeves forming a trocar assembly. An obturator is a removable plug used during insertion of tubular instruments. A trocar assembly is an assembly having a sharp-pointed instrument equipped with a cannula or tube and used to puncture the wall of a body cavity and withdraw fluid. The kit may also include a catheter, an endoscopic surgical instrument, tissue-gripping sleeve members and attachment devices for the trocar sleeves. The kit is packaged in a vacuum-formed enclosure having raised walls which correspond in size and shape to the instruments packaged therein for retaining and displaying the instruments. A method for utilizing the kit is also disclosed. Although Decarie, et al. disclose an endoscopic instrumentation kit and package therefor, the Decarie, et al. patent does not appear to disclose means for attaching the instruments to a surgical field.

Although the prior art approaches recited hereinabove may disclose (1) a surgical drape including a plurality of magnets embedded in the drape to place magnetizable instruments placed on the drape; (2) a securing tape for securing a tubular medical device such as tubing, catheters, intravenous needles, or the like to a patient's skin or to a support; and (3) an endoscopic or laparoscopic instrumentation kit, the prior art recited hereinabove do not appear to disclose the invention described and claimed hereinbelow.

SUMMARY OF THE INVENTION

The present invention addresses the shortcomings of the prior art approaches mentioned hereinabove by providing a surgical appliance kit and system for releasably securing a surgical appliance to a surgical field and a method of assembling the surgical appliance kit.

The surgical appliance kit, system and method reduce the risk that the surgical appliance will slip from the sterilized surgical field and fall to the operating room floor during a surgical procedure. If the surgical appliance were to slip from the sterilized surgical field and fall to the operating room floor, the surgical appliance likely would become contaminated with infectious microbial organisms and may even break. In this case, the surgical appliance must be replaced during the surgical procedure. Replacing the surgical appliance during the surgical procedure increases time to perform the surgical procedure and may even jeopardize the success of the surgical procedure because the surgeon will have become distracted by the need to replace the surgical appliance.

In an exemplary embodiment of the invention, the surgical appliance kit and system comprises a base in the form of a surgical tray on which is disposed one or more surgical appliances. The base is of sufficient rigidity to adequately support the surgical appliances. Typical surgical appliances include scalpels, retractors, forceps, scissors, needle holders, staplers, catheters, and other surgical appliances. A surgical drape also may be disposed on the surgical tray or provided separately.

Also disposed on the surgical tray are at least two attachment members, which are hook-and-loop fasteners. The hook-and-loop fasteners disposed on the surgical tray may be of a type commonly known as Velcro®brand fasteners available from Velcro Industries B.V. located in Amsterdam, The Netherlands. Alternatively, rather than being placed directly on the surgical tray, the hook-and-loop fasteners instead may be contained in a protective, sterilized and sealed container or pouch that is, in turn, disposed on the surgical tray. In other words, the pouch containing the hook-and-loop fasteners is disposed on the surgical tray, rather than the hook-and-loop fasteners being placed directly on the surgical tray. Placement of the hook-and-loop fasteners in the protective pouch provides added assurance that surgical appliances on the surgical tray will not damage the hook-and-loop fasteners prior to use. Each of the hook-and-loop fasteners has an adhesive side for adhesively attaching one of the hook-and-loop fasteners (e.g., a female loop fastener) to the surgical drape and for adhesively attaching another, complementary one of the hook-and-loop fasteners (e.g., a male hook fastener) to the surgical appliance. Alternatively, if desired, the hook-and-loop fastener associated with the surgical drape may be sewn into the surgical drape rather than being adhesively attached to the surgical drape. In any event, the surgical appliance is releasably secured to the surgical drape by engaging the hook-and-loop fastener attached to the surgical appliance with the hook-and-loop fastener attached to the surgical drape.

If desired, a commercially available process indicator strip or tape also may be disposed on the surgical tray. Such a process indicator tape changes color to indicate that contents of the surgical appliance kit were previously exposed to a sterilizing process or agent, such as sterilizing chemicals, heat, sterilizing gas and/or ionizing radiation.

The surgical tray, which has the surgical appliances disposed thereon, is sealingly shrouded by a protective cover. The cover may be a transparent polymer or plastic film material for easily viewing and verifying items disposed on the surgical tray and for protecting contents of the surgical tray from microbial contamination.

During use, according to one exemplary embodiment, the cover is completely or partially removed from the tray. One of the hook-and-loop fasteners is then removed from the tray and adhesively attached to the surgical field defined by the surgical drape that covers the patient. The surgical appliance is retrieved from the tray and the other complementary hook-and-loop fastener is adhesively attached to the surgical appliance. The surgeon or surgeon's assistant then places the surgical appliance on the surgical drape such that the hook-and-loop fastener that was adhesively attached to the surgical drape engages the complementary hook-and-loop fastener that was adhesively attached to the surgical appliance. In this manner, the surgical appliance is releasably secured to the surgical field defined by the surgical drape, so that the surgical appliance is prevented from slipping from the surgical drape and falling to the operating room floor. Also, in this manner, the surgical appliance is simultaneously readily available to the surgeon during the surgical procedure because the surgical appliance is releasably secured to the surgical field near the surgeon.

Thus, use of the surgical appliance kit, system and method disclosed herein prevents disruption in the surgical procedure that might otherwise be caused by the need to replace a fallen surgical appliance and reduces health risk to the patient by maintaining the surgeon's attention focused on the exacting surgical procedure being performed.

According to an aspect of the present invention, there is provided a surgical appliance kit for releasably securing a surgical appliance to a surgical field, comprising: a base adapted to have the surgical appliance disposed thereon; a plurality of attachment members adapted to be disposed on the base, the plurality of attachment members being adapted to releasably secure the surgical appliance to the surgical field; and a cover attached to the base and adapted to cover the surgical appliance and the plurality of attachment members.

According to another aspect of the present invention, there is provided a surgical appliance kit for releasably securing a surgical appliance to a surgical field, comprising: a base defining a cavity adapted to receive the surgical appliance therein; a first attachment pad and a second attachment pad received in the cavity, the first attachment pad defining a first surface having a hook configuration and the second attachment pad defining a second surface having a loop configuration; and a cover attached to the base and adapted to cover the surgical appliance, the first attachment pad and the second attachment pad.

According to yet another aspect of the present invention there is provided a surgical appliance kit for releasably securing a surgical appliance to a surgical field, comprising: a base defining a cavity adapted to receive the surgical appliance therein; a first attachment pad and a second attachment pad received in the cavity, the first attachment pad having a first surface defining a hook configuration and having a first adhesive portion adhesively attachable to the surgical appliance, the second attachment pad having a second surface defining a loop configuration for cooperatively engaging the hook configuration defined by the first surface and having a second adhesive portion adhesively attachable to the surgical field; and a cover attached to the base and adapted to sealingly cover the surgical appliance, the first attachment pad and the second attachment pad for protecting the surgical appliance, the first attachment pad and the second attachment pad from contamination.

According to still another aspect of the present invention there is provided a surgical appliance system for releasably securing a surgical appliance to a surgical field, comprising: a base adapted to have the surgical appliance disposed thereon; a plurality of attachment members adapted to be disposed on the base, the plurality of attachment members being adapted to releasably secure the surgical appliance to the surgical field; and a cover attached to the base and covering the surgical appliance and the plurality of attachment members.

According to a further aspect of the present invention, there is provided a container for containing a plurality of attachment members, comprising: a pouch defining an interior volume therein for receiving the plurality of attachment members, the pouch having a sealed access end portion; and a pair of opposing flaps integrally connected to the sealed access end portion of the pouch for unsealing and opening the sealed access end portion of the pouch, whereby the plurality of attachment members are retrievable from the interior volume as the sealed access end portion of the pouch is unsealed and opened.

According to an additional aspect of the present invention there is provided a method of assembling a surgical appliance kit for securing a surgical appliance to a surgical field, comprising: providing a base; disposing the surgical appliance on the base; disposing a plurality of attachment members on the base, the plurality of attachment members being adapted to releasably secure the surgical appliance to the surgical field; attaching a cover to the base; and covering the surgical appliance and the plurality of attachment members with the cover.

A feature of the present invention is the provision of a plurality of attachment members comprising hook-and-loop fasteners adapted to releasably secure the surgical appliance to the surgical field.

Another feature of the present invention is the provision of a protective pouch containing the plurality of attachment members.

In addition to the foregoing, various other method and/or device aspects and features are set forth and described in the teachings, such as text (e.g., claims and/or detailed description) and/or drawings of the present invention.

The foregoing is a summary and thus may contain simplifications, generalizations, inclusions, and/or omissions of detail. Consequently, those skilled in the art will appreciate that the summary is illustrative only and is not intended to be in any way limiting. In addition to the illustrative aspects, embodiments, and features described hereinabove, further aspects, embodiments, and features will become apparent by reference to the drawings and the following detailed description.

BRIEF DESCRIPTION OF THE DRAWINGS

The invention will be more fully understood by reference to the detailed description in conjunction with the following figures, wherein:

FIG. 19 is a cross-sectional view in partial elevation of a first alternative attachment member, wherein the first alternative attachment member is sewn into the surgical drape, this view also showing the surgical appliance manually separated from the surgical drape;

DETAILED DESCRIPTION OF PREFERRED EMBODIMENTS

Figure 1:
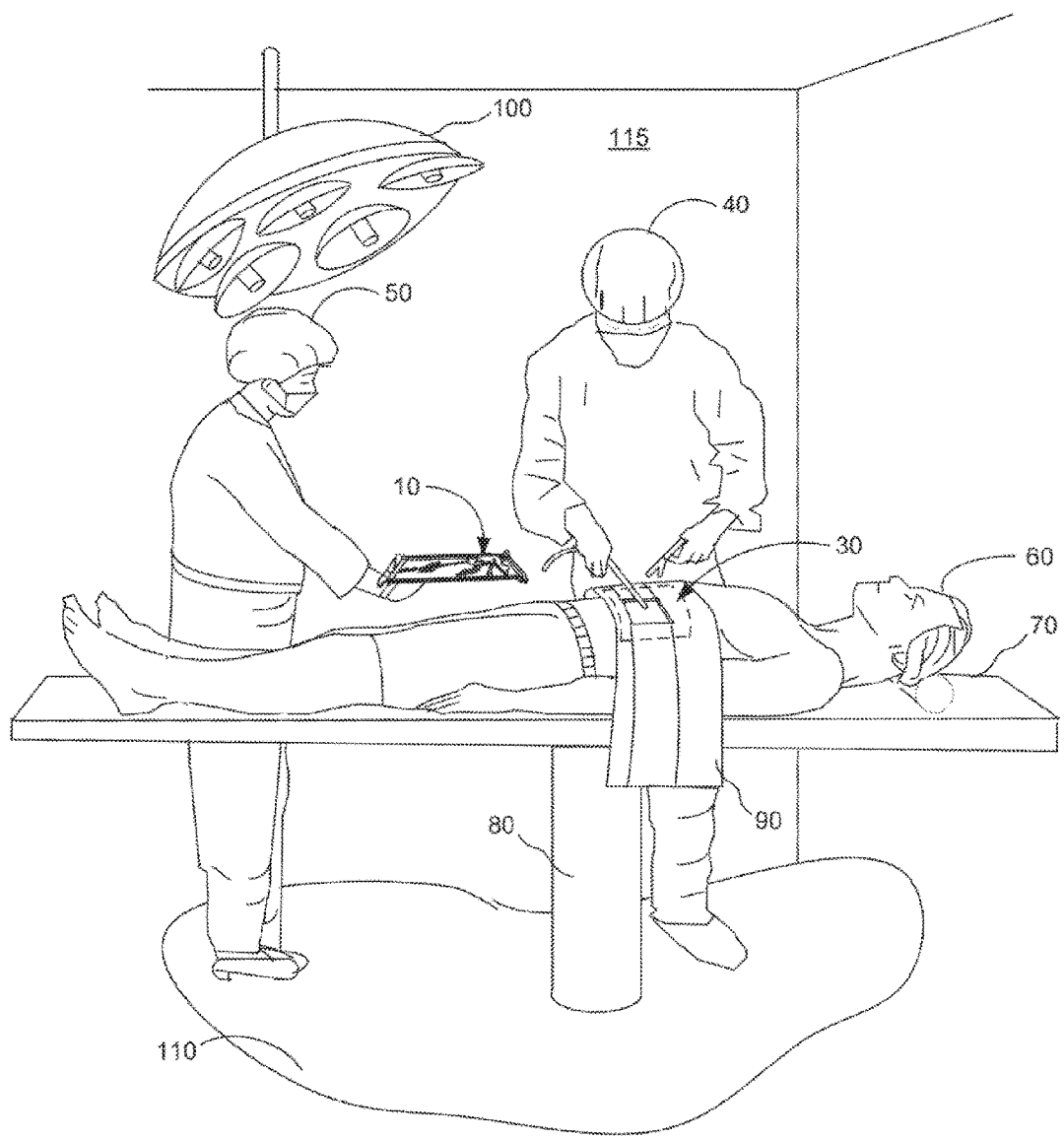
FIG. 1 is a view in perspective of a first embodiment surgical appliance kit and system for releasably securing a surgical appliance to a surgical field defined by a surgical drape, this view also showing an operating room in which a surgeon is performing a surgical procedure on a patient with the first embodiment surgical appliance kit and system nearby.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from either the spirit or scope of the invention.

In addition, the present patent specification uses formal outline headings for clarity of presentation. However, it is to be understood that the outline headings are for presentation purposes, and that different types of subject matter may be discussed throughout the application (e.g., device(s)/structure(s) may be described under process(es)/operations heading(s) and/or process(es)/operations may be discussed under structures)/process(es) headings; and/or descriptions of single topics may span two or more topic headings). Hence, the use of the formal outline headings is not intended to be in any way limiting.

Therefore, with reference to FIGS. 1 and 2, there is shown a first embodiment surgical appliance kit and system, generally referred to as 10 (hereinafter referred to as "first embodiment kit 10"), for releasably securing a surgical appliance 20 to a surgical field, generally referred to as 30. The surgical field 30 is an operating field that is an isolated area where an invasive procedure or surgery is performed and that must be kept sterile by aseptic techniques. In the several figures, surgical field 30 is shown delimited by a plurality of dotted lines in the form of a polygon. However, surgical field 30 may be any suitable size and shape, such as circular, that is required by the surgical procedure being performed.

Referring to FIGS. 1, 2, 2A, 2B, 2C, 2D, 2E, 2F, 2G, 2H, 2I and 2J, and by way of example only, and not by way of limitation, surgical appliance 20 may be selected from a plurality of suitable surgical appliances depending on the surgical procedure being performed. For example, surgical appliance 20 may be a surgical stapler for closing an incision. In this regard, the stapler may be a commercially available stapler such as the "ECHELON FLEX™ Powered ENDOPATH® Stapler" available from Ethicon Endo Surgery, Incorporated located in Cincinnati, Ohio, U.S.A. However, it should be appreciated that surgical appliance 20 may be any one of other possible commercially available surgical appliances, such as a scalpel for making incisions, retractor for holding open a portion of the body, forceps for holding organs and tissue, scissors for suturing and cutting, needle holder for holding needles while suturing tissue, catheter for allowing drainage or administration of fluids, as well as other surgical appliances. As shown in the several figures and by way of illustration only, such other surgical appliances or instruments include, but are not limited to, an electro-surgical cauterization appliance 32a, a scalpel appliance 32b, a bipolar radiofrequency appliance 32c, a suction appliance 32d, biopsy forceps 32e, bandage and plaster shears 32f, an orthopedic chisel appliance 32g, a lung retractor appliance 32h, a laryngeal forceps appliance 321 or a tongue depressor appliance 32j.

With particular reference to FIG. 1, first embodiment kit 10 is presented to a surgeon 40 by a surgical assistant, such as a circulating nurse 50. Circulating nurse 50 is located sufficiently near surgeon 40, so that surgical appliance 20 is readily accessible by surgeon 40 for performing an invasive surgical procedure on a patient 60. Patient 60, who is shown lying on an operating table 70 supported by a support column 80, is completely or partially covered by at least one commercially available surgical drape 90. Surgical drape 90 is sterilized linen that is placed on patient 60 in a manner that delineates surgical field 30. In this regard, surgical drape 90 may be a film-based composite or nonwoven fabric, such as a laminate comprising polypropylene fibers and a polyethylene film and may contain fluid collection pouches (not shown) and fluid absorbent areas for collecting body fluids. Such a surgical drape laminate material reduces risk of inadvertent strike-through by sharps (e.g., needles and scalpels) during surgery. A suitable surgical drape 90 may be a commercially available surgical drape, such as the "3M™ Steri-Drape™ 9000 Surgical Drape", which may be available from 3M Company located in St. Paul. Minn., U.S.A.

Referring again to FIG. 1, surgical field 30 is preferably illuminated by a light source 100. The light source 100, which forms no part of the present invention, provides necessary illumination to surgical field 30, so that surgeon 40 can adequately view surgical field 30 during the surgical procedure. An operating room floor 110, which is part of an operating room environment 115, extends beneath circulating nurse 50, surgeon 40 and support column 80. Although appropriate steps are taken to sterilize operating environment 115, floor 110 may nonetheless contain pathogens and microbial organisms thereon, such as *clostridia, streptococci, staphylococci, E. coli bacilli* and other pathogens and microbial organisms that can lead to the previously mentioned post-operative, nosocomial health complications, such as hepatitis, bronchitis, sepsis from intravenous sites, and other health complications. Therefore, it is important that at no time should surgical appliance 20 contact floor 110.

Figure 2:
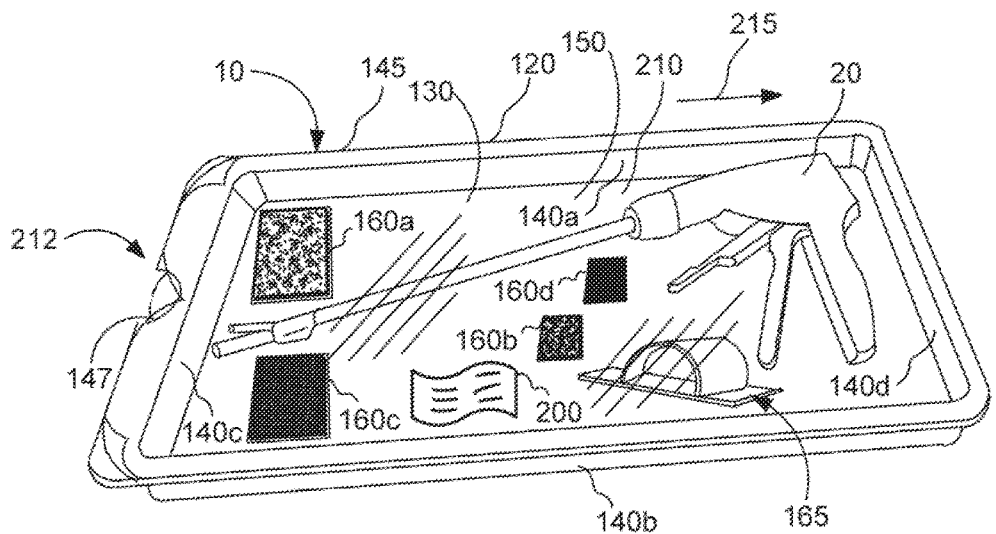
FIG. 2 is a view in perspective of the first embodiment surgical appliance kit and system, the first embodiment surgical appliance kit and system including a surgical appliance, such as a surgical stapler.
Figure 2A:
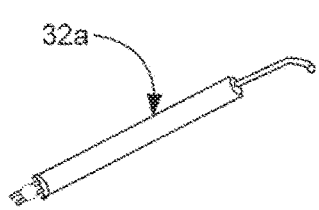
FIG. 2A shows the surgical appliance as an electrosurgical cauterization appliance.
Figure 2B:
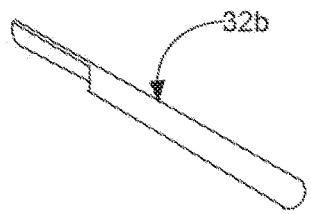
FIG. 2B shows the surgical appliance as a scalpel appliance.
Figure 2C:
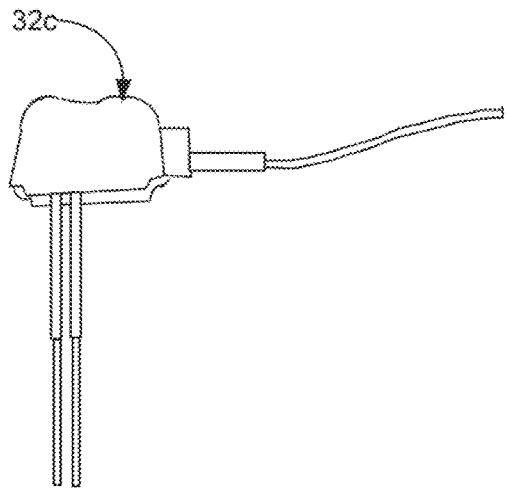
FIG. 2C shows the surgical appliance as a bipolar radiofrequency appliance.
Figure 2D:
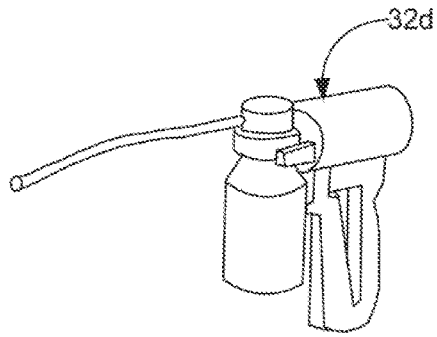
FIG. 2D shows the surgical appliance as a suction appliance.
Figure 2E:
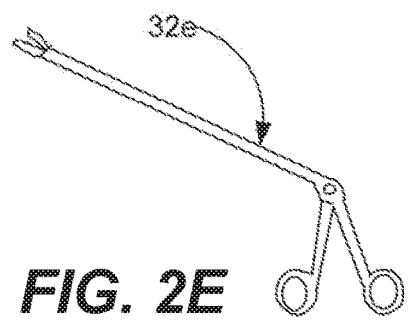
FIG. 2E shows the surgical appliance as a biopsy forceps appliance.
Figure 2F:
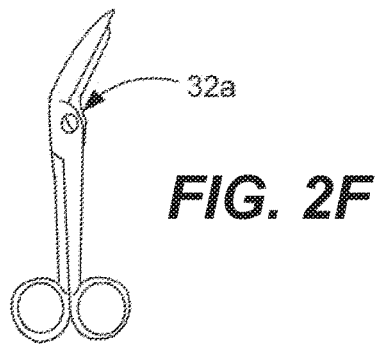
FIG. 2F shows the surgical appliance as a bandage and plaster shears appliance.
Figure 2G:
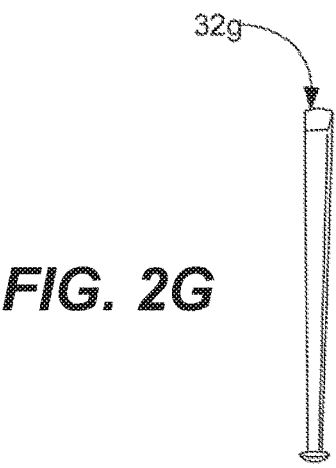
FIG. 2G shows the surgical appliance as an orthopedic chisel appliance.
Figure 2H:
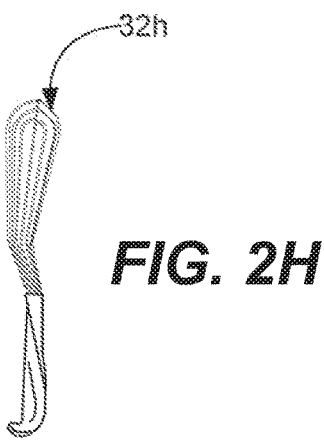
FIG. 2H shows the surgical appliance as a lung retractor appliance.
Figure 2I:
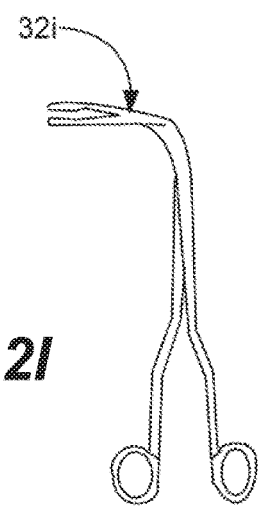
FIG. 2I shows the surgical appliance as a laryngeal forceps appliance.
Figure 2J:
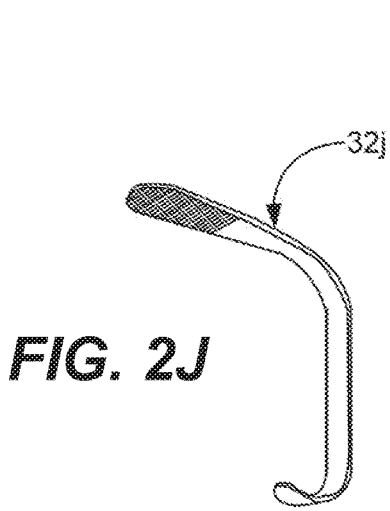
FIG. 2J shows the surgical appliance as a tongue depressor appliance.

As best seen in FIG. 2, first embodiment kit 10 comprises a light-weight and portable base in the form of a surgical tray 120 that includes a planer centerboard 130. Centerboard 130 may be made of any suitably rigid material, such as a sufficiently rigid metal, plastic polymer, or the like for adequately supporting surgical appliance 20 thereon. More specifically, centerboard 130 may be a metal, such as stainless steel or aluminum, or a plastic polymer, such as polypropylene. A first sidewall 140a, a second sidewall 140b, a front wall 140c and a rear wall 140d upwardly rise from centerboard 130 and are integrally connected thereto. First sidewall 140a, second sidewall 140b, front wall 140c and rear wall 140d may be made of the same rigid material as centerboard 130 to facilitate manufacture of surgical tray 120, such as by a metal stamping process or a plastic mold process, as the case may be. First sidewall 140a is parallel to second sidewall 140b and front wall 140c is parallel to rear wall 140d. First sidewall 140a and second sidewall 140b perpendicularly intersect front wall 140c and rear wall 140d and are integrally connected thereto. In addition, first sidewall 140a, second sidewall 140b, front wall 140c and rear wall 140d beneficially define a flanged perimeter, lip or rim 145 extending along first sidewall 140a, second sidewall 140b, front wall 140c and rear wall 140d. Rim 145 defines a cut-out 147 therein for reasons provided hereinbelow. Rim 145 has particular utility for purposes of the invention, as described in detail hereinbelow. Also, the configuration of centerboard 130, first sidewall 140a, second sidewall 140b, front wall 140c and rear wall 140d results in surgical tray 120 being configured as a polygon that is generally square or generally rectangular in shape. However, surgical tray 120 may be any suitable shape other than generally square or rectangular, such as generally circular or generally oval in shape. Moreover, surgical tray 120 need not include first sidewall 140a, second sidewall 140b, front wall 140c and rear wall 140d, if desired. In this case, only a planer support is present, as described in a separate embodiment of the surgical tray, which separate embodiment of the surgical tray is presented hereinbelow. It should be appreciated that centerboard 130, first sidewall 140a, second sidewall 140b, front wall 140c and rear wall 140d define a cavity 150 in surgical tray 120 for receiving surgical appliance 20. Therefore, surgical appliance 20 is received in cavity 150 while surgical appliance 20 is disposed on and supported by centerboard 130. Consequently, any of the configurations mentioned hereinabove results in surgical tray 120 functioning as a light-weight and portable carrying means for carrying first embodiment kit 10 into operating room 115 and for presentment of first embodiment kit 10 to surgeon 40.

Figure 3:
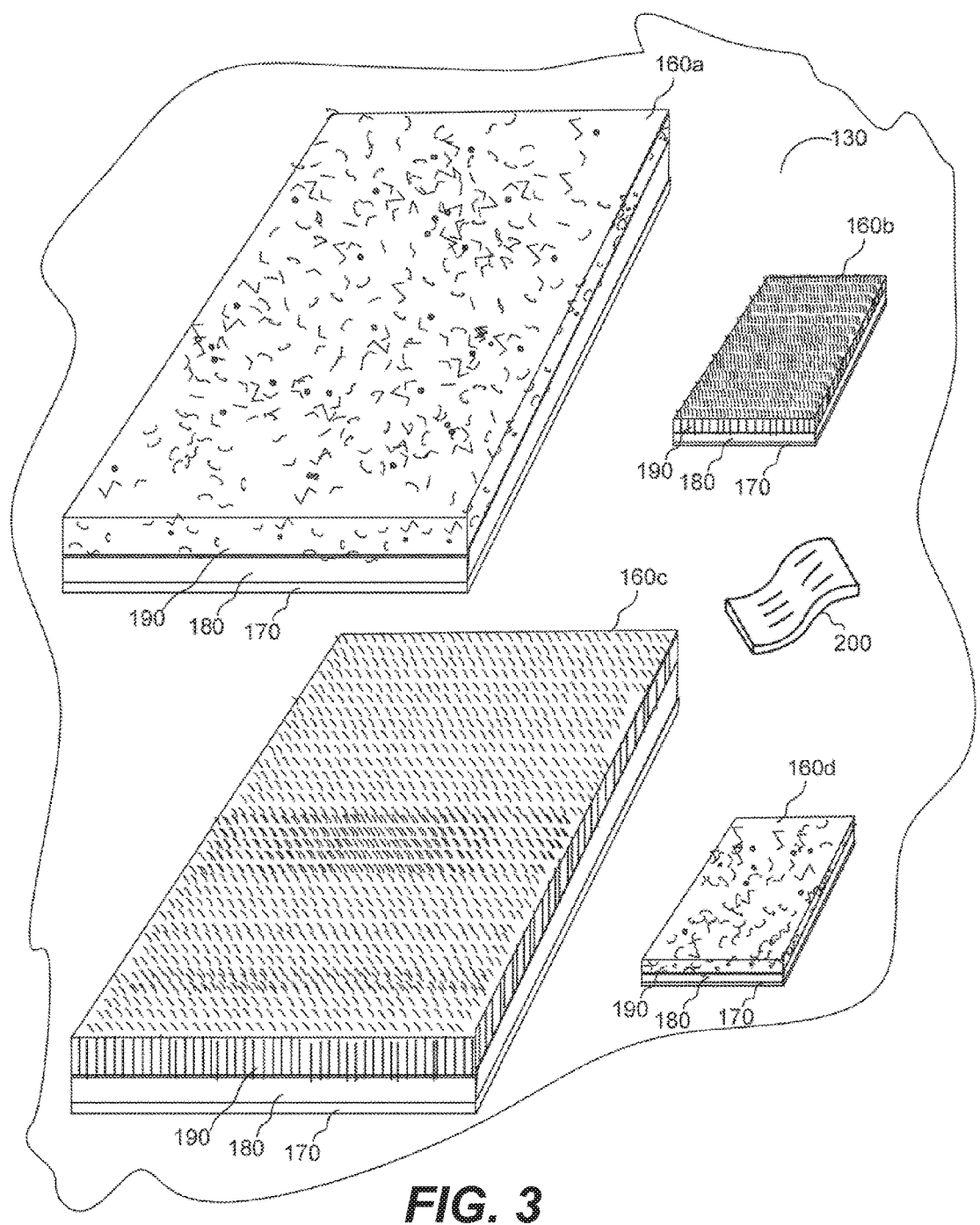
FIG. 3 is a fragmentary view in perspective of a plurality of attachment members of various sizes and a chemical process indicator strip belonging to the first embodiment surgical appliance kit and system.
Figure 3A:
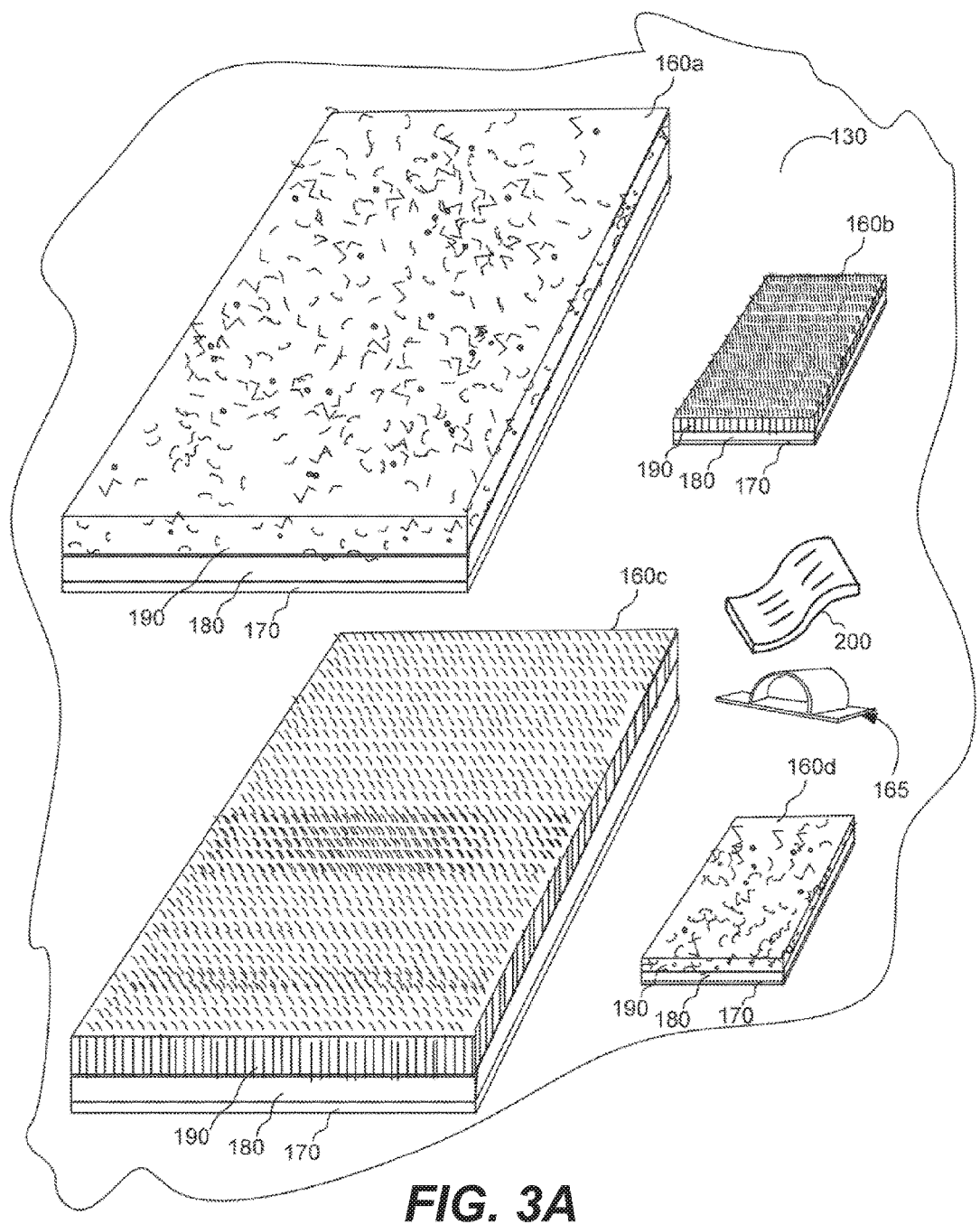
FIG. 3A is a fragmentary view in perspective of a plurality of attachment members of various sizes, a chemical process indicator strip and a tube secuing strip belonging to the first embodiment surgical appliance kit and system.

Referring to FIGS. 2, 3 and 3A, in addition to surgical appliance 20, first embodiment kit 10 comprises a plurality of attachment members, such as first attachment member 160a, second attachment member 160b, third attachment member 160c and fourth attachment member 160d disposed on centerboard 130, for reasons disclosed hereinbelow. Each attachment member 160a/b/c/d comprises a plurality of layers or laminates stacked one upon the other. More specifically, each attachment member 160a/b/c/d comprises a first laminate 170. The first laminate 170 is a flexible protective plastic sheeting material that is manually peeled away and discarded prior to using attachment members 160a/b/c/d. A second laminate 180 comprises an adhesive. The adhesive is a pressure sensitive "peel and stick" adhesive, such as a water-based acrylic adhesive. In this regard, the adhesive may be the "Velcro® brand 72" water-based acrylic pressure sensitive adhesive available from Velcro Industries B.V. located in Amsterdam, The Netherlands. With respect to first attachment member 160a and fourth attachment member 160d, layered on second laminate 180 is a third laminate 190, which has a female "loop" configuration. Third laminate 190 comprises either Nylon, polyester, or the like. Also, with respect to second attachment member 160b and third attachment member 160c, layered on second laminate 180 is third laminate 190, but of a different configuration. That is, third laminate 190 that belongs to second attachment member 160b and third attachment member 160c has a male "hook" configuration. The hook-and-loop construction mentioned immediately hereinabove allow the plurality of attachment members 160a/b/c/d to be releasably interlocked. A hook-and-loop cord or tube securing strip, generally referred to as 165, is also disposed in cavity 150 for reasons provided hereinbelow. In this regard, the plurality of attachment members 160a/b/c/d and securing strip 165 may be commercially available hook-and-loop fasteners, tapes or pads, such as Velcro® brand fasteners available from Velcro Industries B.V.

Referring again to FIGS. 2, 3 and 3A, if desired, a commercially available chemical process indicator tape or strip 200 also may be disposed on centerboard 130 that belongs to surgical tray 120. Such a process indicator strip 200 changes color to indicate that contents of first embodiment kit 10 were previously exposed to a sterilizing process or agent, such as sterilizing chemicals, heat, sterilizing gas and/or ionizing radiation. For example, the chemical process strip melts and changes color when subjected to sufficient sterilizing heat in order to indicate that a sterilizing heat process was performed. In the case of gaseous ethylene oxide, process indicator strip 200 comprises a reagent that contains a hydrochloric acid salt of a basic substance together with a pH indicator. The hydrochloric acid salt of the basic substance is reacted with the ethylene oxide to remove the hydrochloric acid. The remaining basic substance reacts with the pH indicator to cause the color change. A commercially available process indicator strip for monitoring sterilization parameters in steam cycles and ethylene oxide may be the "STERIS Verify® Chemical Indicator and Integrator" available from Steris Corporation located in Mentor, Ohio, U.S.A.

As best seen in FIG. 2, cavity 150 that is defined by surgical tray 120 is shrouded by a cover 210 sealingy attached to previously mentioned rim 145 of surgical tray 120. Cover 210 may be heat-sealed to rim 145 or adhesively sealed to rim 145, such that environmental contaminants are prevented from entering cavity 150. Cover 210 may be a clear, translucent or transparent polymer or plastic film material for easily viewing and verifying items disposed on surgical tray 120. In addition, cover 210 is sufficiently strong for preventing puncture thereof by sharps that may be contained in cavity 150. For example, cover 210 may be made from strong, clear, low density polyethylene or polypropylene plastic of suitable thickness, such as about 2 millimeters (i.e., 0.0787 inch) thick.

Referring again to FIGS. 1 and 2, portable first embodiment kit 10 is presented to surgeon 40 by circulating nurse 50 who is standing near surgeon 40. Surgeon 40 and/or circulating nurse 50 verifies the necessary contents of first embodiment kit 10 by viewing the contents of first embodiment kit 10 through transparent cover 210. In addition, surgeon 40 or circulating nurse 50 verifies that the contents of first embodiment kit 10 were previously subjected to a sterilization process by observing the color of process strip 200, if process strip 200 is present. Surgeon 40 or the circulating nurse 50 then removes transparent cover 210 from rim 145 of surgical tray 120 by accessing a portion of cover 210 through cut-out 147 and manually pulling cover 210 away from cut-out 147 in the direction of an arrow 212. In this regard, cover 210 is pulled toward rear wall 140d in the general direction of arrow 215, until cover 210 is sufficiently detached from rim 145. Cavity 150 becomes exposed as cover 210 is sufficiently detached from rim 145, so that contents of surgical tray 120 become accessible to surgeon 40 and/or to circulating nurse 50.

Referring to FIGS. 1, 2, and 3, surgeon 40 or circulating nurse 50 manually removes first laminate 170 from adhesive second layer 180 of first attachment member 160a and adhesively attaches first attachment member 160a to surgical field 30. Thereafter, surgeon 40 or circulating nurse 50 manually removes first laminate 170 from adhesive second layer 180 of second attachment member 160b and adhesively attaches second attachment member 160b to surgical appliance 20. Alternatively, fourth attachment member 160d may be adhesively attached to a separate surgical appliance (not shown) and third attachment member 160c may be adhesively attached to surgical drape 90, if necessary, for adhesively attaching an additional, separate surgical appliance to surgical drape 90.

Before surgery, surgical appliance 20, having fourth attachment member 160d adhesively attached thereto, is manually aligned with first attachment member 160a that is adhesively attached to surgical drape 90. Surgical appliance 20 is then firmly pressed against first attachment member 160a. Pressing surgical appliance 20 against first attachment member 160a causes the female loops of third laminate 190 that belongs to first attachment member 160a to intimately engage the male hooks of third laminate 190 that belongs to fourth attachment member 160d. In this manner, surgical appliance 20 is releasably attached to surgical drape 90 and is immobile on surgical drape 90 until needed by surgeon 40.

During surgery, surgeon 40 grasps surgical appliance 20 and lifts surgical appliance 20 away from first attachment member 160a. When this occurs, the hooks belonging to third laminate 190 of fourth attachment member 160d disengage the loops belonging to third laminate 190 of first attachment member 160a. When using this first embodiment kit 10, first attachment member 160a remains adhesively attached to surgical drape 90 and fourth attachment member 160d remains adhesively attached to surgical appliance 20. In this manner, surgical appliance 20 is separated from surgical drape 90, so that surgical appliance 20 can be used for surgery. Moreover, first embodiment kit 10 allows surgical appliance 20 to be repeatedly removed from and reattached to surgical drape 90, as necessary, during the surgical procedure due to the hook-and-loop configuration of attachment members 160a/160d. However, at no time is surgeon's 40 eyesight diverted from the surgical procedure being performed.

Although not critical, it is nonetheless important that fourth attachment member 160d that is attached to surgical appliance 20 not be too large in length and width. If fourth attachment member 160d is too large, the gripping power required to lift surgical appliance 20 from its temporarily secured position will become so great that it will lift surgical drape 90 that is present on patient 60. Therefore, fourth attachment member 160d should be sufficiently large to securely hold surgical appliance 20 to surgical drape 90, but not so large as to lift drape 90 when surgical appliance 20 is removed from its temporary holding position. In this regard, width of fourth attachment member 160d may be between about $\frac{1}{8}^{th}$ inch and about $\frac{3}{8}^{th}$ inch with a preferred width of about $\frac{1}{4}^{th}$ inch. Length of fourth attachment member 160d is sufficient to allow easy attachment to surgical appliance 20 coupled with cooperating with the width dimension to assure that surgical appliance 20 will be secured to surgical drape 90 and can be removed without substantially lifting surgical drape 90. A slight lifting of surgical drape 90 is allowable. In addition, if the holding strength is too great, surgical appliance 20 will not become separated from surgical drape 90 and first attachment member 160a.

Figure 4:
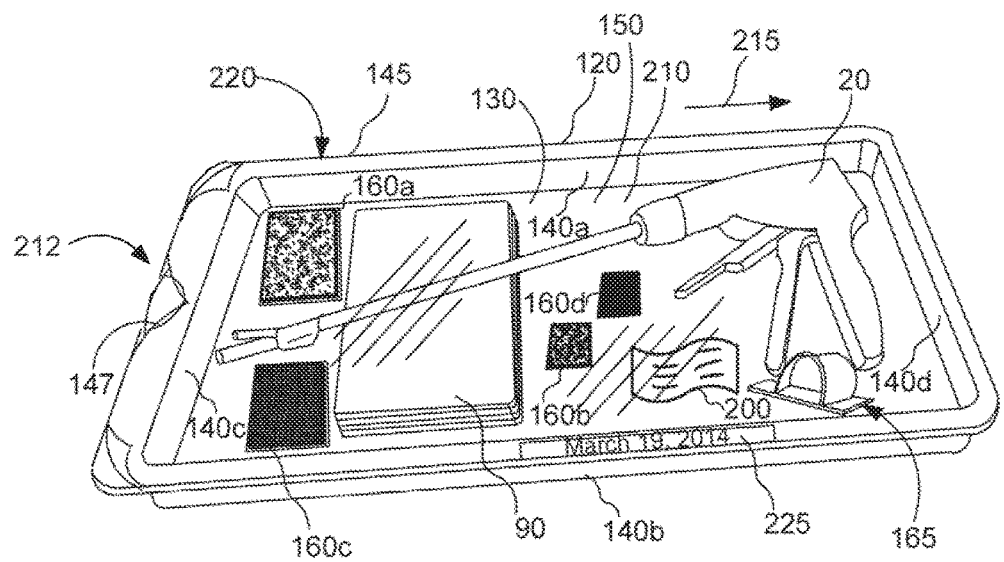
FIG. 4 is a view in perspective of a second embodiment surgical appliance kit and system, this view showing that the second embodiment surgical appliance kit and system includes a tube securing strip and an externally disposed expiration date strip.
Figure 4A:
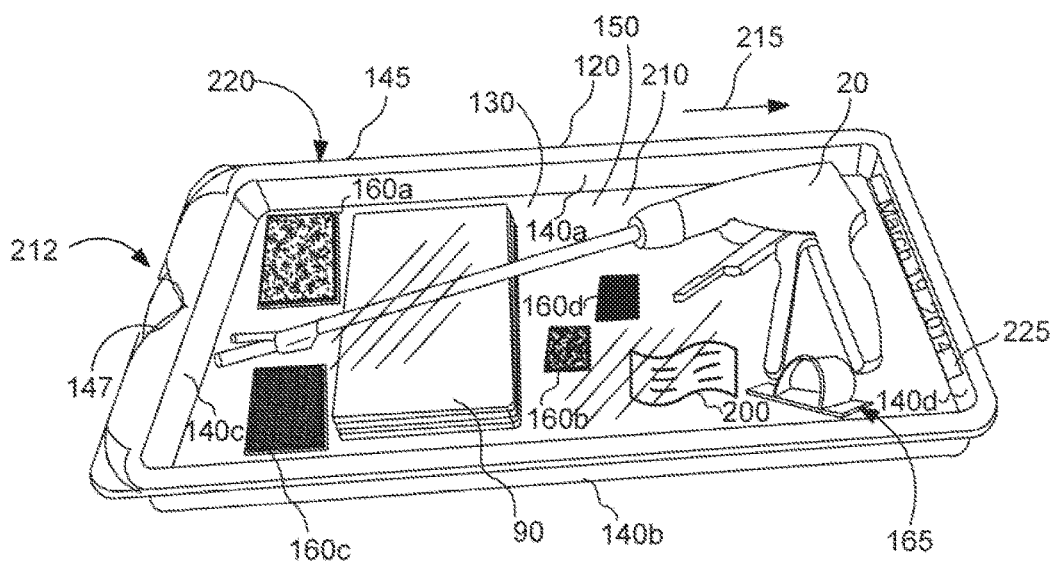
FIG. 4A is a view in perspective of the second embodiment surgical appliance kit and system, this view showing that the second embodiment surgical appliance kit and system includes a tube securing strip and an internally disposed expiration date strip.

Turning now to FIGS. 4 and 4A, there is shown a second embodiment surgical appliance kit and system, generally referred to as 220 (hereinafter referred to as "second embodiment kit 220"), for releasably securing surgical appliance 20 to surgical field 30. Second embodiment kit 220 is substantially similar to first embodiment kit 10, except second embodiment kit 220 includes surgical drape 90 disposed in cavity 150 that is defined by surgical tray 120. Thus, in this embodiment, surgical drape 90 is included with surgical tray 120 rather than being separately provided. Including surgical drape 90 with surgical tray 120 provides a convenient package of pre-sterilized items needed for the surgical procedure. In addition, an expiration tape or date strip 225 is adhered to an exterior surface of surgical tray 120, such as on the rim or perimeter 145 of surgical tray 120 for identifying the date contents of surgical tray 120 should no longer be considered sterile. Alternatively, expiration date strip 225 may be adhered to an interior surface of surgical tray 120, such as on rear wall 140d of surgical tray 120. Date strip 225 includes an adhesive backing for adhering date strip 225 either to the exterior surface or interior surface of surgical tray 120.

Figure 5:
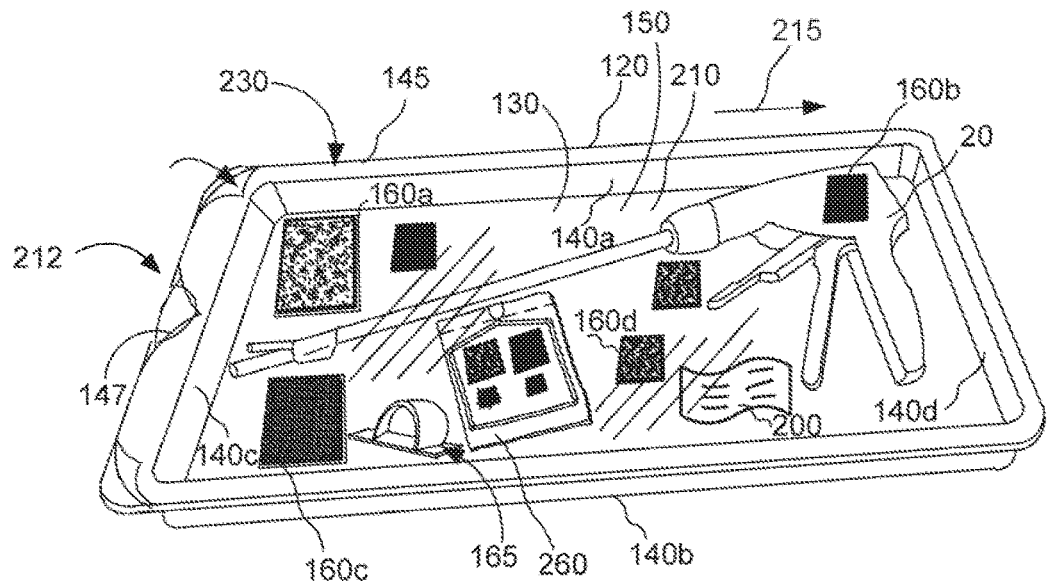
FIG. 5 is a view in perspective of a third embodiment surgical appliance kit and system.

In FIG. 5, there is shown a third embodiment surgical appliance kit and system, generally referred to as 230 (hereinafter referred to as "third embodiment kit 230"), for releasably securing surgical appliance 20 to surgical field 30. Third embodiment kit 230 is substantially similar to second embodiment kit 220, except second attachment member 160b is already adhesively attached to surgical appliance 20. Therefore, in this case, first laminate 170 was previously removed from second attachment member 160b. Pre-attaching second attachment member 160b to surgical appliance 20 saves time during the surgical procedure because first laminate 170 need not be peeled away from second attachment member 160b prior to beginning the surgical procedure or during the surgical procedure.

Figure 6:
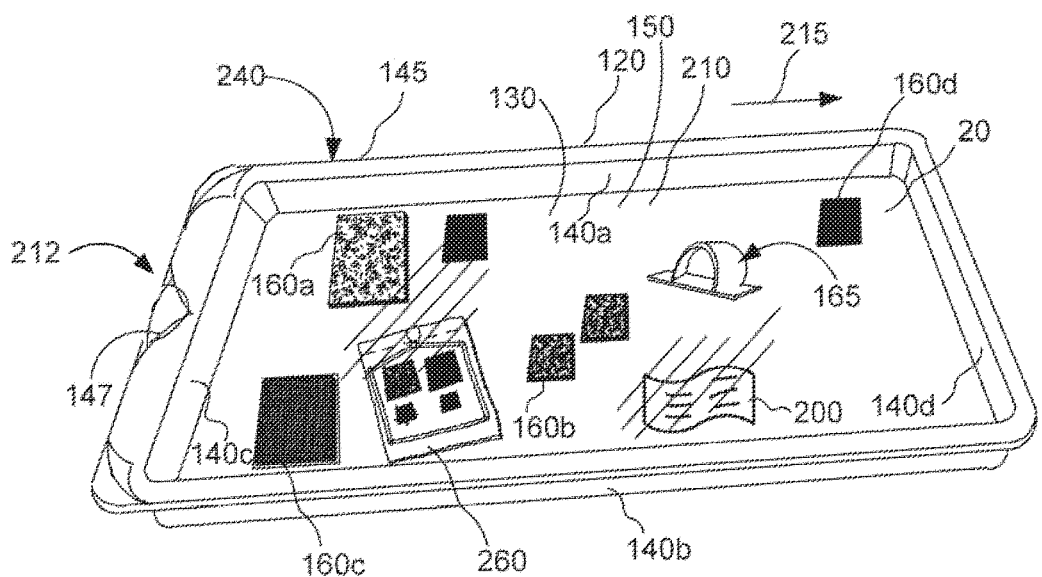
FIG. 6 is a view in perspective of a fourth embodiment surgical appliance kit and system.

Referring to FIG. 6, there is shown a fourth embodiment surgical appliance kit and system, generally referred to as 240 (hereinafter referred to as "fourth embodiment kit 240"), for releasably securing surgical appliance 20 to surgical field 30. Fourth embodiment kit 240 is substantially similar to third embodiment kit 230, except surgical drape 90 is absent from cavity 150 because surgical drape 90 is provided separately.

Figure 7:
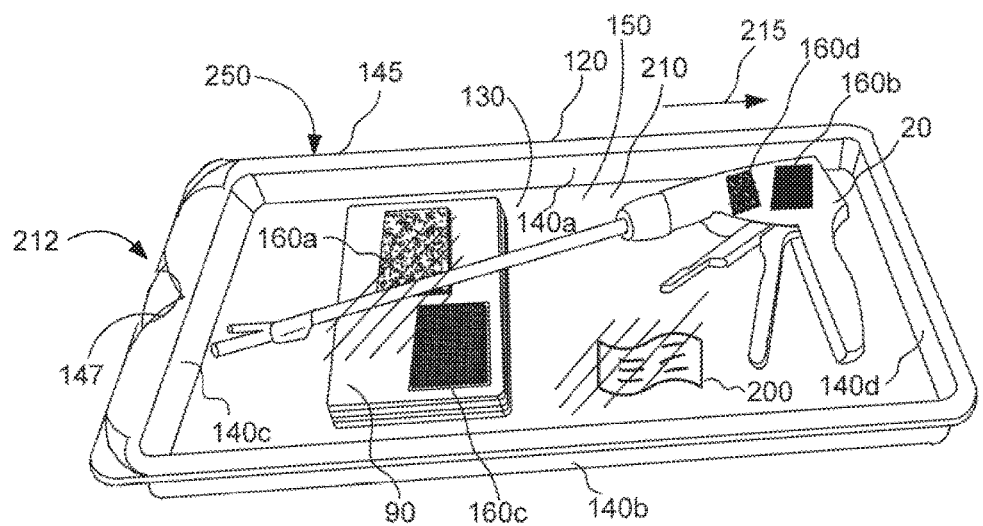
FIG. 7 is a view in perspective of a fifth embodiment surgical appliance kit and system.

With reference to FIG. 7, there is shown a fifth embodiment surgical appliance kit and system, generally referred to as 250 (hereinafter referred to as "fifth embodiment kit 250"), for releasably securing surgical appliance 20 to surgical field 30. Fifth embodiment kit 250 is substantially similar to second embodiment kit 220, except first attachment member 160a and third attachment member 160c are already adhesively attached to surgical drape 90 that is disposed in cavity 150. Also, second attachment member 160b and fourth attachment member 160d are already adhesively attached to surgical appliance 20. Therefore, in this case, first laminate 170 was previously removed from first attachment member 160a, second attachment member 160b, third attachment member 160c and fourth attachment member 160d. Pre-attaching first attachment member 160a and third attachment member 160c to surgical drape 90 and pre-attaching second attachment member 160b and fourth attachment member 160d to surgical appliance 20 saves time during the surgical procedure because first attachmaent member 160a and third attachment member 160c were pre-attached to surgical drape 90 and because second attachment member 160b and fourth attachment member 160d were pre-attached to surgical appliance 20, prior to beginning the surgical procedure.

Figure 8:
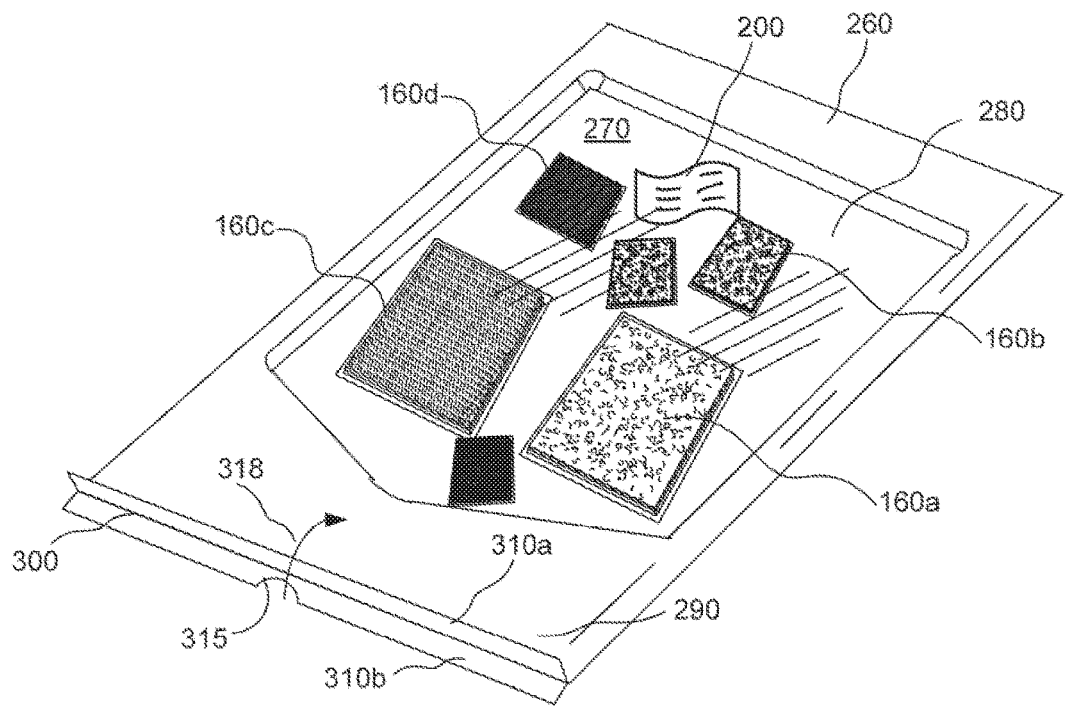
FIG. 8 is a view in perspective of a protective pouch containing a plurality of attachment members, the pouch having a pair of opposing flaps for opening a sealed end of the pouch.
Figure 9:
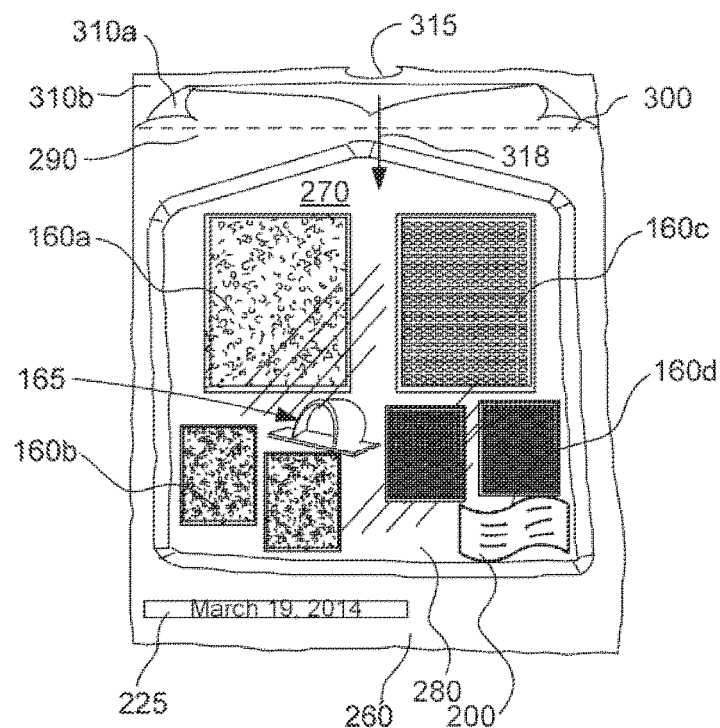
FIG. 9 is a plan view of the pouch containing the plurality of attachment members, this view also showing one of the pair of opposing flaps being pulled-backwardly to unseal and open the sealed end of the pouch.
Figure 10:
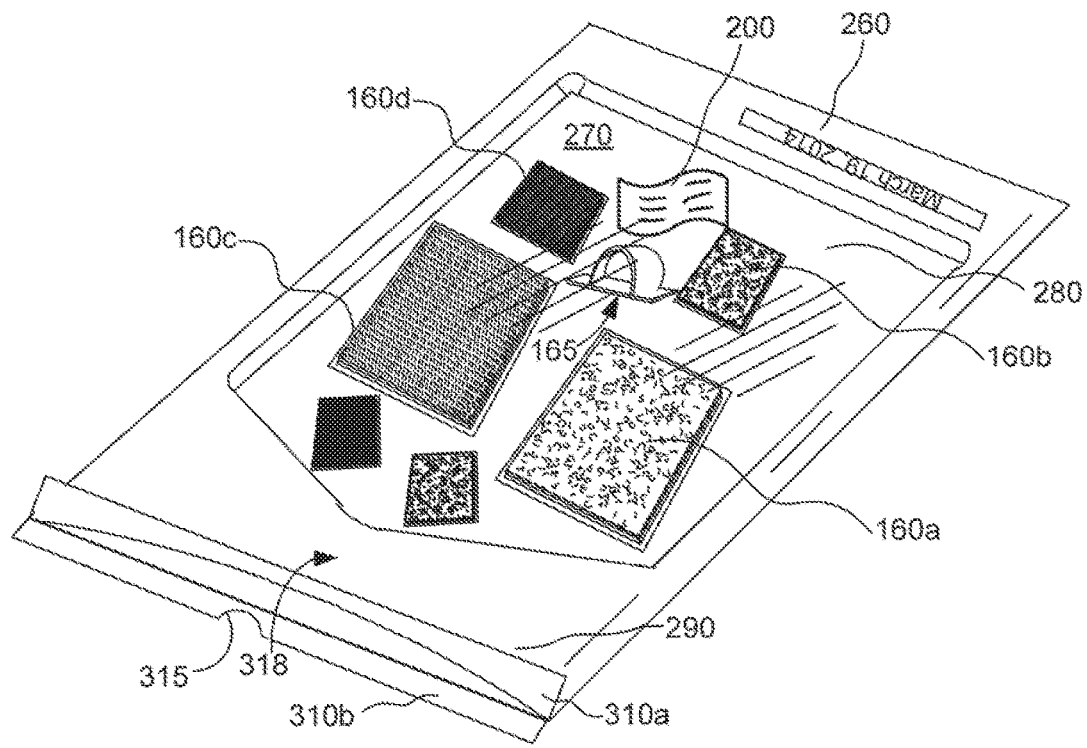
FIG. 10 is a view in perspective of the pouch containing the plurality of attachment members, this view also showing the sealed end of the pouch having been unsealed and opened by means of the flaps.

Referring to FIGS. 8, 9 and 10, a container in the form of a closed protective pouch 260 may be provided for containing attachment members 160a/b/c/d and for avoiding contact between attachment members 160a/b/c/d and items in cavity 150, such as sharps, that might otherwise damage attachment members 160a/b/c/d. In other words, placement of attachment members 160a/b/c/d in protective pouch 260 provides added assurance that items on the surgical tray will not damage attachment members 160a/b/c/d prior to use.

Referring again to FIGS. 8, 9 and 10, pouch 260 defines an interior volume 270 containing attachment members 160a/b/c/d and a process indicator strip 200. Thus, there are two process indicator strips 200 present. One process indicator strip 200 is disposed directly on centerboard 130 for indicating that items in cavity 150 were exposed to a pre-sterilization process and the other process indicator strip 200 is disposed in interior volume 270 for indicating that attachment members 160a/b/c/d were exposed to a pre-sterilization process. Also disposed in pouch 260 may be previously mentioned tube securing strip 165. Pouch 260, which is hermetically sealed, may be made of a puncture-resistant polymer plastic material. Pouch 260 may also include a clear, translucent or transparent polymer plastic window portion 280 integrally formed therewith for viewing and verifying presence of attachment members 160a/b/c/d color of process indicator strip 200, and tube securing strip 165. Although pouch 260 is initially hermetically sealed, pouch 260 nonetheless includes a sealed access end portion 290 that can be unsealed and opened for providing access to interior volume 270. Access end portion 290 may be heat sealed, such as along a seam 300. A pair of opposing, bendable pull-tabs 310a and 310b outwardly extend from seam 300 for reasons provided presently. Thus, pull-tabs 310a and 310b are integrally connected to access end portion 290. Pull-tab 310b may define a cut-out 315 therethrough for reasons disclosed momentarily. In this regard, while holding pull-tab 310b, pull-tab 310a is most easily grasped with fingers passing through cut-out 315. Pull-tab 310a is then manually pulled generally in the direction of an arrow 318 with sufficient force, such that seam 300 is separated or opened. Opening of seam 300 allows access to interior volume 270 for removing attachment members 160a/b/c/d and tube securing strip 165 from interior volume 270. After removal from interior volume 270, attachment members 160a/b/c/d and securing strip 165 then become available for adhesive attachment to surgical drape 90 and/or surgical appliance 20.

Figure 11:
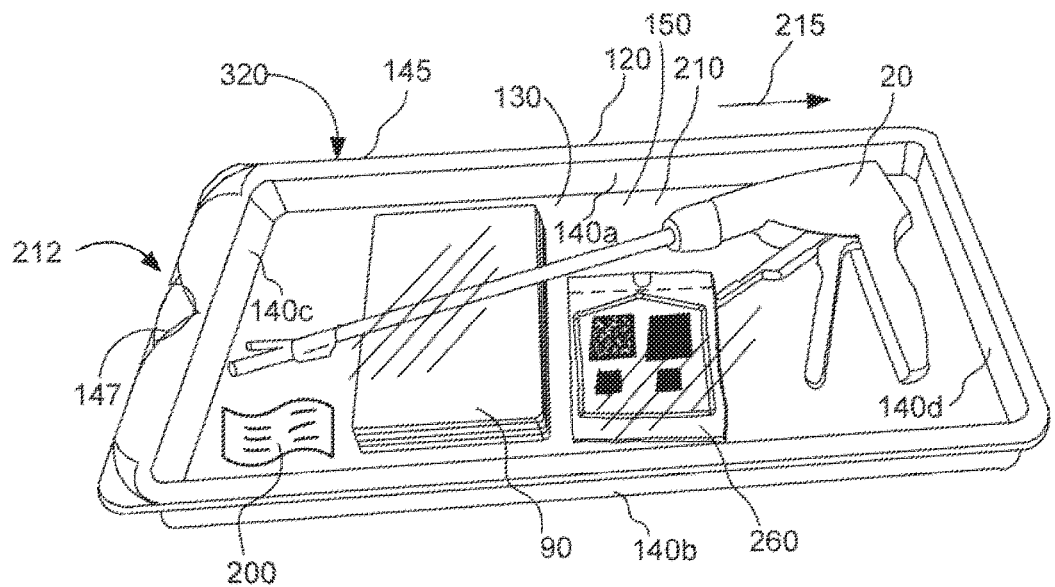
FIG. 11 is a view in perspective of a sixth embodiment surgical appliance kit and system.

With reference to FIG. 11, there is shown a sixth embodiment surgical appliance kit and system, generally referred to as 320 (hereinafter referred to as "sixth embodiment kit 320"), for releasably securing surgical appliance 20 to surgical field 30. Sixth embodiment kit 320 is substantially similar to fifth embodiment kit 250, except previously mentioned pouch 260 is placed in cavity 150 that is defined by surgical tray 120.

Figure 12:
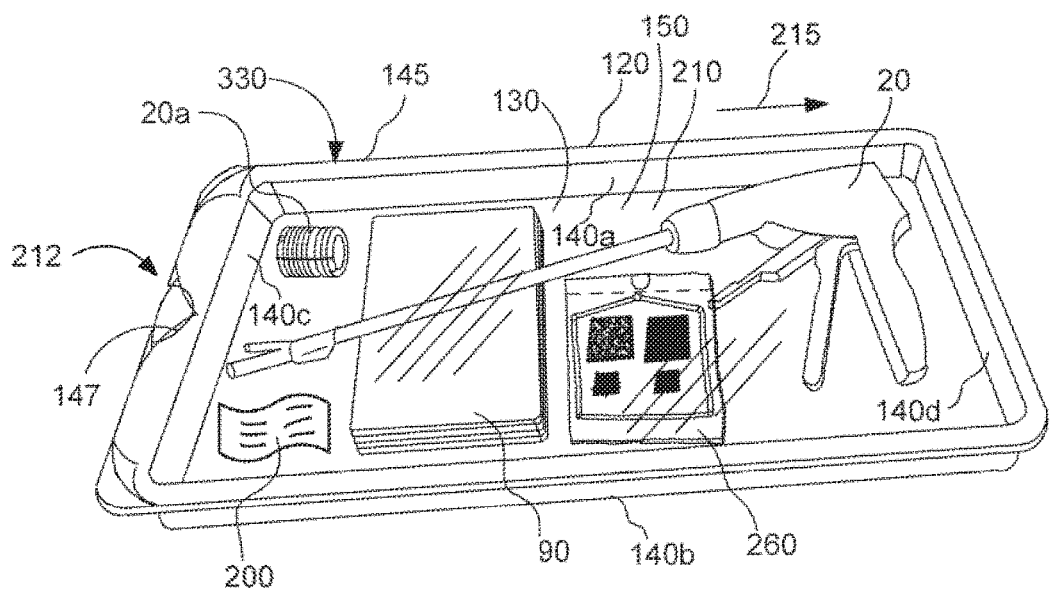
FIG. 12 is a view in perspective of a seventh embodiment surgical appliance kit and system including a plurality of surgical appliances, such as a coiled catheter and the surgical stapler.

Referring to FIG. 12, there is shown a seventh embodiment surgical appliance kit and system, generally referred to as 330 (hereinafter referred to as "seventh embodiment kit 330"), for releasably securing surgical appliance 20 to surgical field 30. Seventh embodiment kit 330 is substantially similar to sixth embodiment kit 320, except a plurality of surgical appliances are disposed on surgical tray 120, such as surgical stapler 20 and a wound or coiled catheter 20a, as shown.

Figure 13:
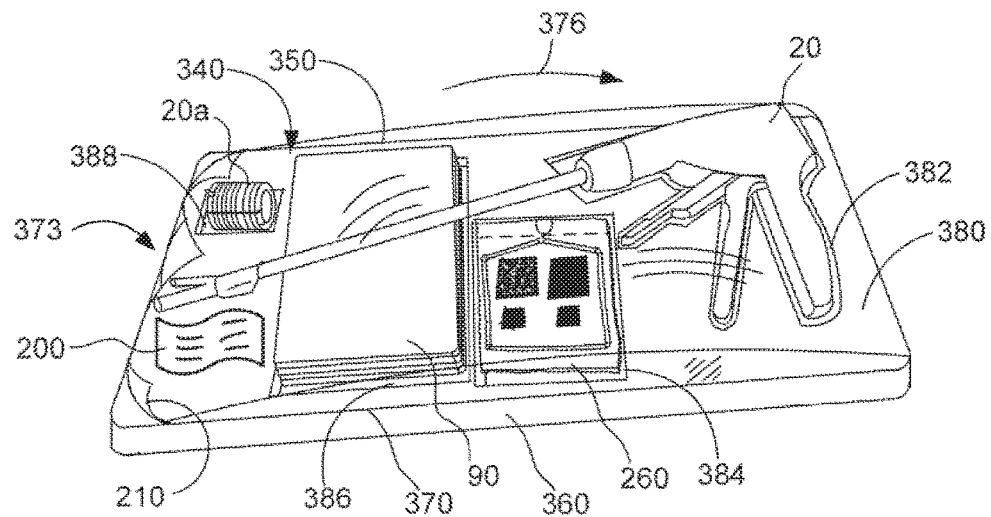
FIG. 13, is a view in perspective of an eighth embodiment surgical appliance kit and system.

Referring to FIG. 13, there is shown an eighth embodiment surgical appliance kit and system, generally referred to as 340 (hereinafter referred to as "eighth embodiment kit 340"), for releasably securing surgical appliance 20 or coiled catheter 20a to surgical field 30. According to this embodiment, a second embodiment surgical tray 350 includes a planar support 360 having a peripheral edge 370 therearound. Previously mentioned cover 210 is sealingly attached to peripheral edge 370 and covers the contents of second embodiment surgical tray 350. Cover 210 is sealingly attached to peripheral edge 360 by being heat sealed to peripheral edge 360 or by being adhesively attached to peripheral edge 360. Cover 210 is removed from second embodiment surgical tray 350 by being manually peeled away from peripheral edge 370 generally in the direction of arrows 373 and 376. An upper surface 380 of planer support 360 defines a plurality of wells or recesses therein, such as a first recess 382, a second recess 384, a third recess 386 and a fourth recess 388. First recess 382, second recess 384, third recess 386 and fourth recess 388 conform to the shape of the stapler surgical appliance 20, pouch 260, surgical drape 90 and the coiled catheter surgical appliance 20a, respectively. Therefore, recesses 382/384/386/388 are of a predetermined contour and are of sufficient depth to maintain the stapler surgical appliance 20, pouch 260, surgical drape 90 and the coiled catheter surgical appliance 20a substantially immobile on upper surface 380, so that these items do not collide with each other and become damaged while eighth embodiment kit 340 is transported to and deployed in operating room environment 115.

Figure 14:
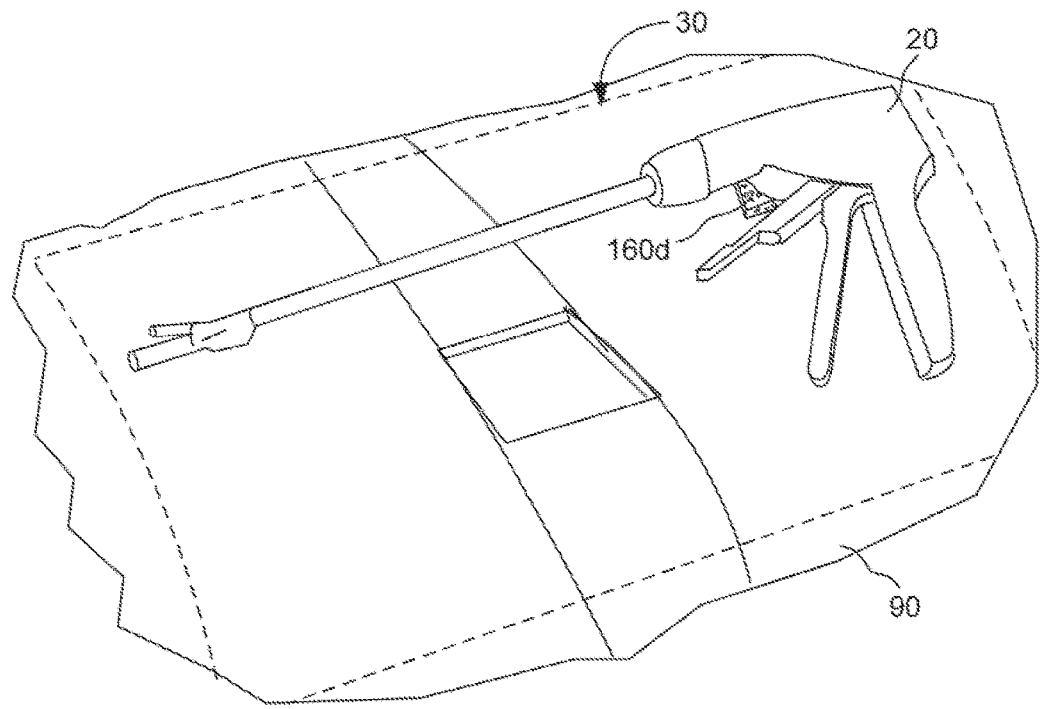
FIG. 14 is a fragmentary view in perspective of a surgical appliance releasably secured to the surgical field defined by the surgical drape, the surgical appliance being releasably secured to the surgical field by a first arrangement of the attachment members.
Figure 15:
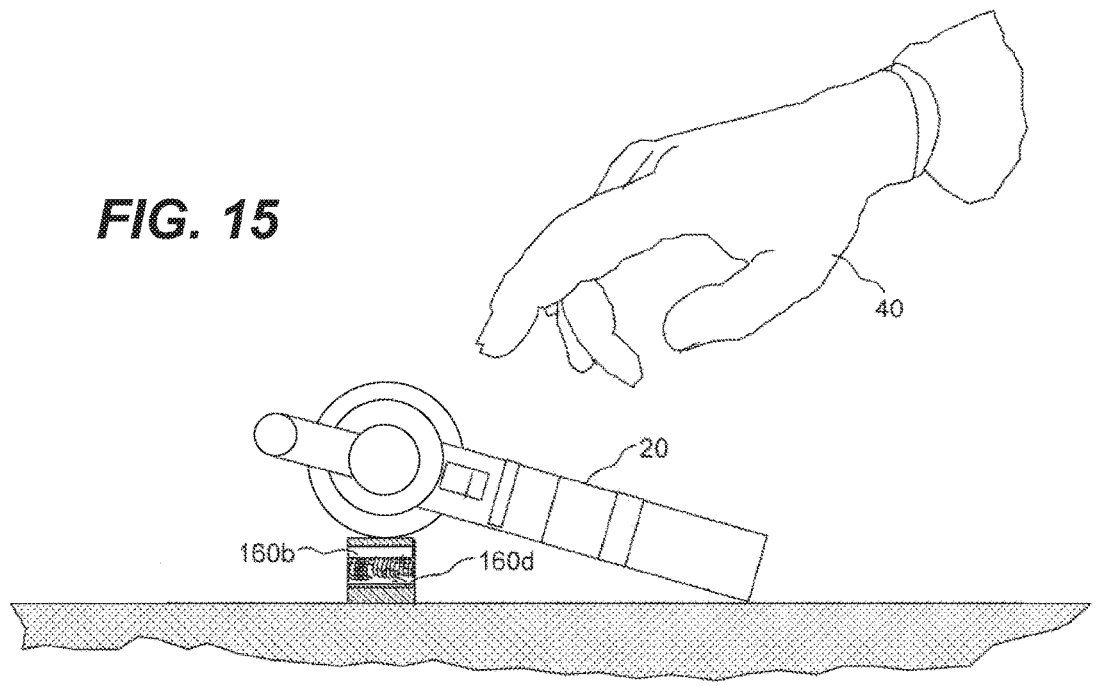
FIG. 15 is a cross-sectional view in partial elevation of the surgical appliance releasably secured to the surgical field defined by the surgical drape, the surgical appliance being releasably secured to the surgical field by the first arrangement of the attachment members.

Referring to FIGS. 14 and 15, surgical appliance 20 is shown releasably secured to surgical field 30 by a first arrangement of attachment members comprising a relatively small male "hook" attachment member 160b that is adhesively attached to surgical appliance 20 and that intimately engages a relatively small female "loop" attachment member 160d that is adhesively attached to surgical field 30.

Figure 16:
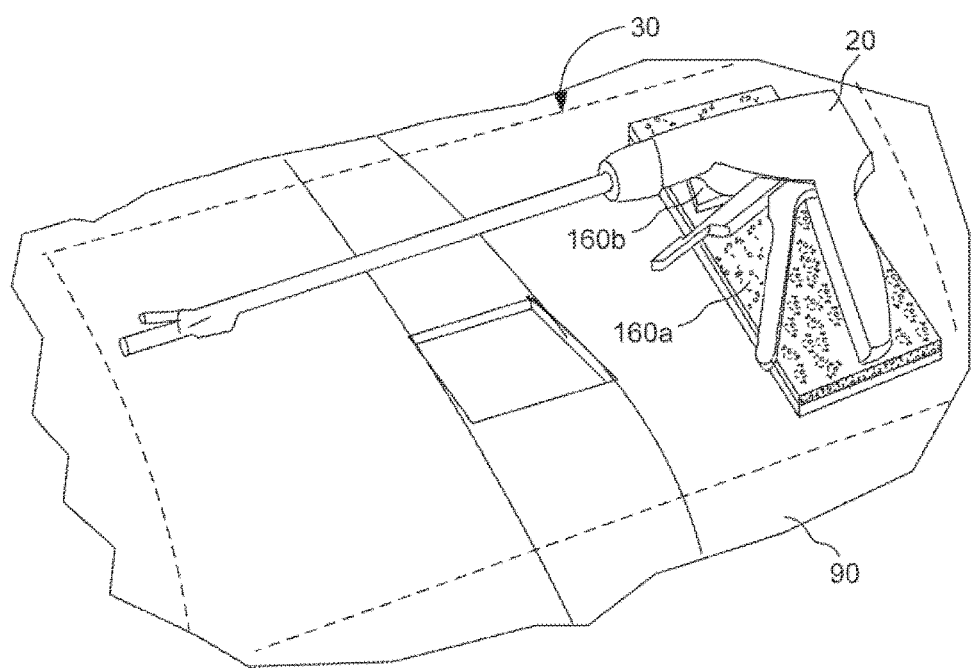
FIG. 16 is a fragmentary view in perspective of the surgical appliance releasably secured to the surgical field defined by the surgical drape, the surgical appliance being releasably secured to the surgical field by a second arrangement of the attachment members.
Figure 17:
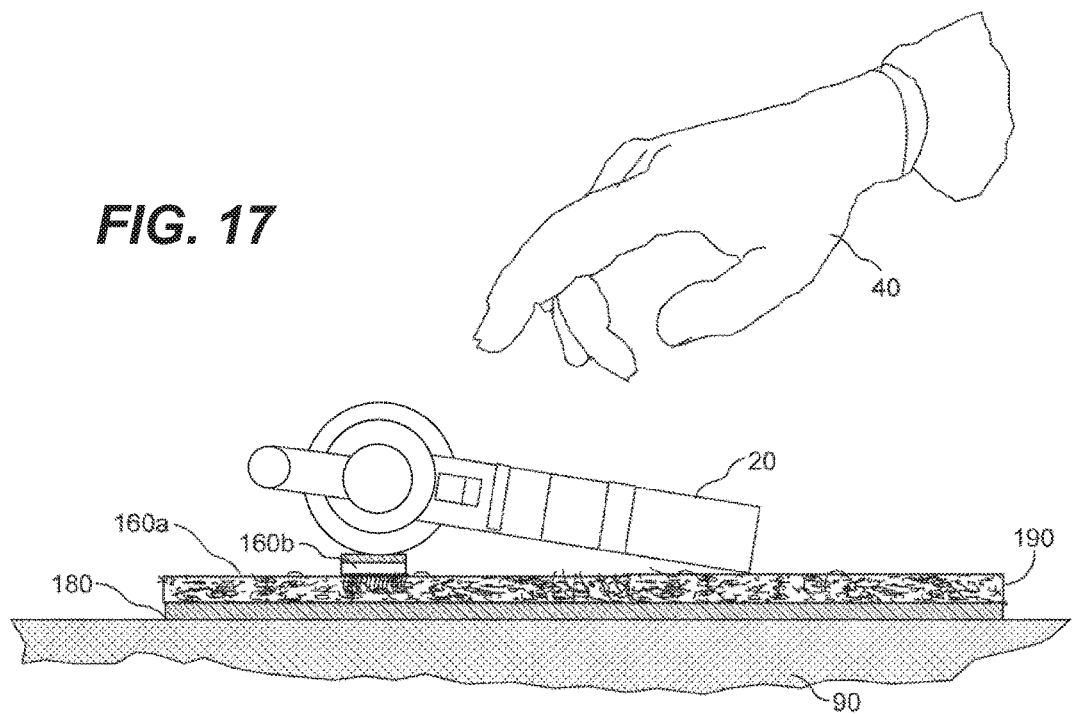
FIG. 17 is a cross-sectional view in partial elevation of the surgical appliance releasably secured to the surgical field defined by the surgical drape, the surgical appliance being releasably secured to the surgical field by the second arrangement of the attachment members.
Figure 18:
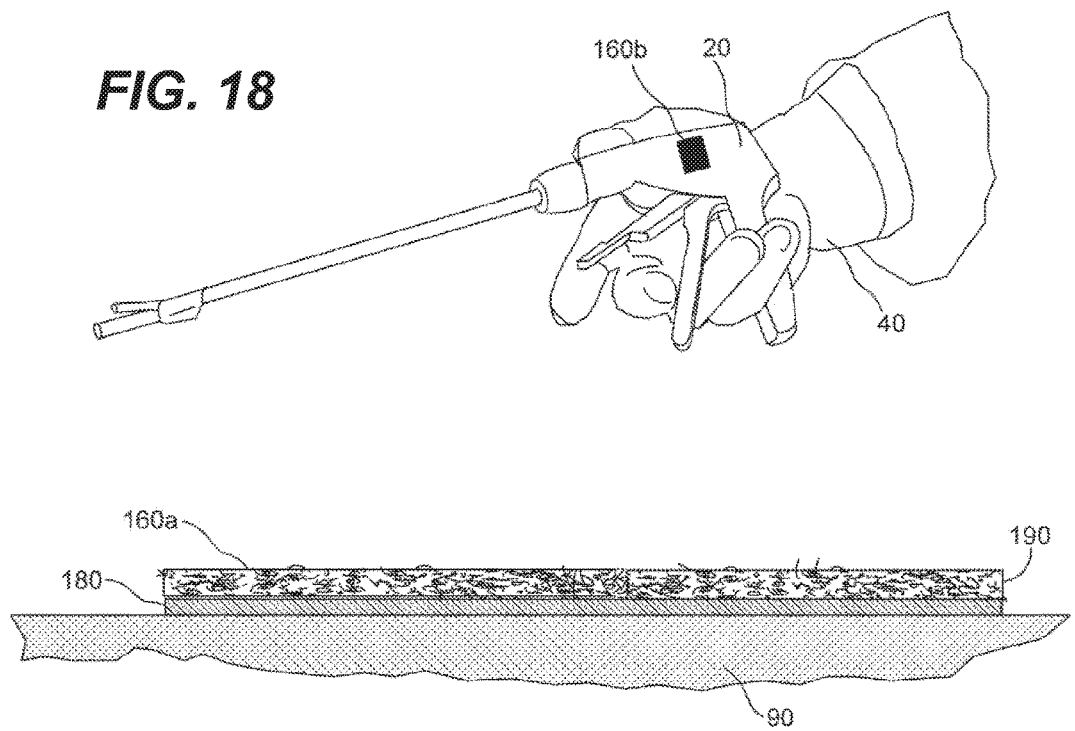
FIG. 18 is a cross-sectional view in partial elevation of the surgical appliance manually separated from the surgical drape by means of the second arrangement of the attachment members.

With reference to FIGS. 16, 17 and 18, surgical appliance 20 is shown releasably secured to surgical field 30 by a second arrangement of attachment members comprising a relatively small male "hook" attachment members 160b that is adhesively attached to surgical appliance 20 and that intimately engages a relatively larger female "loop" attachment member 160a that is adhesively attached to surgical field 30. Relatively larger attachment member 160a has a relatively larger adhesive surface area. The relatively larger adhesive surface area provides added assurance attachment member 160a will remain affixed to surgical drape 90 during the surgical procedure.

Referring to FIG. 19, a first alternative attachment member 390 is adapted to be sewn into surgical drape 90 by a plurality of threads 400. First alternative attachment member 390 comprises previously mentioned third laminate 190. Threads 400 interconnect any portion of third laminate 190 and surgical drape 90. In other words, first alternative attachment member 390 is integrally connected to surgical drape 90 by threads 400 prior to surgeon 40 beginning the surgical procedure, such as during manufacture of surgical drape 90. In this regard, surgical drape 90, which has first alternative attachment member 390 sewn therein, may be provided separately or included with any of the surgical kit embodiments described herein.

Figure 20:
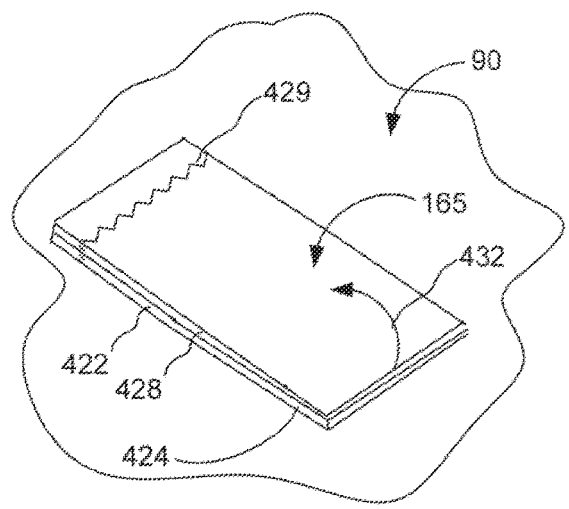
FIG. 20 is a view in perspective of a second alternative attachment member for releasably securing a tubular surgical appliance, such as a catheter, to the surgical field defined by the surgical drape.
Figure 20A:
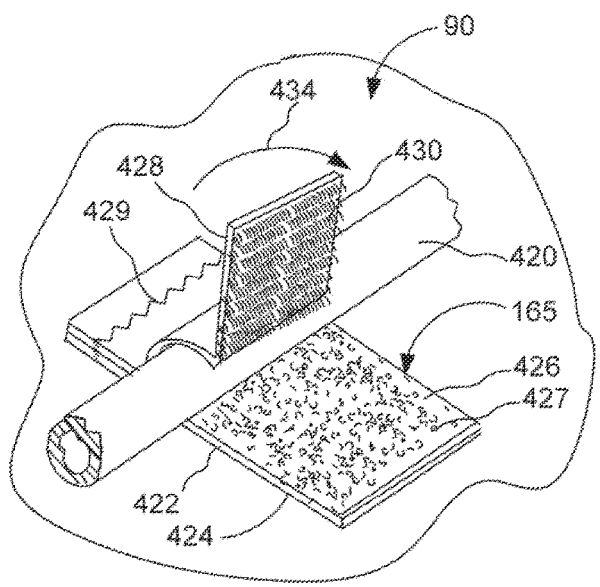
FIG. 20A is a view in perspective of the second alternative attachment member operatively positioned to secure the tubular surgical appliance to the surgical drape.
Figure 20B:
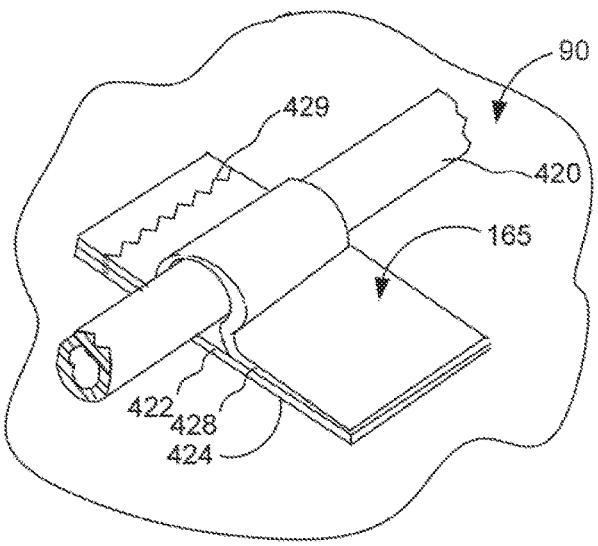
FIG. 20B is a view in perspective of the second alternative attachment member having secured the tubular surgical appliance to the surgical drape.

Referring to FIGS. 20, 20A and 20B, previously mentioned electrical cord or tube securing strip 165, which forms a second alternative attachment member, is adapted to secure a tubular member 420, such as a catheter, to surgical field 30. Rather than securing a catheter to surgical field 30, securing strip 165 also may be used to secure an electrical cord to surgical field 30, which electrical cord may be attached to surgical appliance 20 to electrically operate surgical appliance 20. Securing the electrical cord to surgical field 30 reduces the risk that such an electrical cord will move to obstruct and otherwise interfere with the surgical procedure. More specifically, tube securing strip 165 comprises a first strip layer 422. The first strip layer 422 has an adhesive underside surface 424 that allows securing strip 165 to be adhesively attached to surgical drape 90. A top-side surface 426 of first strip layer 422 includes a multiplicity of loop-configured elements 427, such as found in Velcro® brand fasteners. Securing strip 165 further comprises a second strip layer 425 connected to first strip layer 422, such as by stitching 429. Second strip layer 425 includes a multiplicity of hook-configured elements 430 capable of releasably engaging loop-configured elements 427. Securing strip 165 is used to secure tubular member 420 to surgical drape 90 by adhesively attaching securing strip 165 to surgical drape 90. In this regard, second strip layer 428 is peeled or separated from engagement with first strip layer 422 such as in the direction of an arrow 432. Tubular member 420 is then placed onto top-side surface 426. Nexzt, second strip layer 428 is laid over an exterior of tubular member 420, such as in the direction of an arrow 434. Hook-configured elements 430 are then reengaged with loop-configured elements 427.

Figure 21:
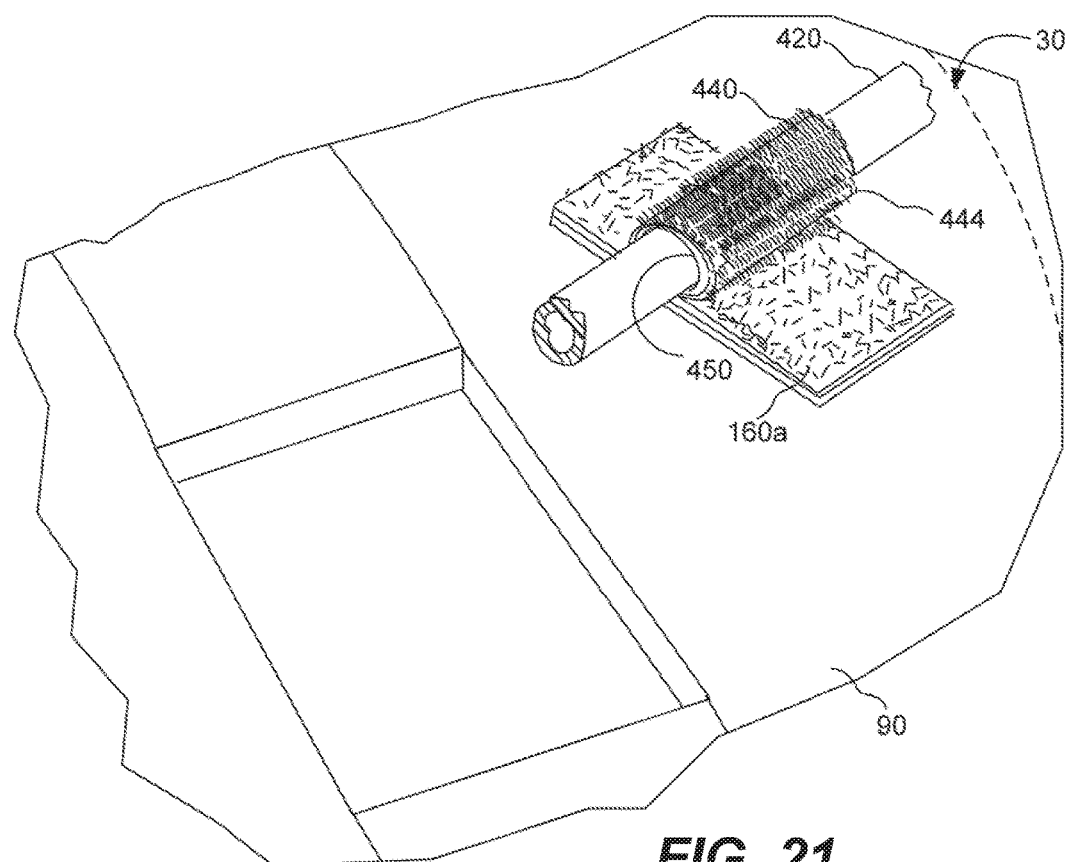
FIG. 21 is a view in perspective of a third alternative attachment member releasably securing a tubular surgical appliance, such as a catheter, to the surgical field defined by the surgical drape.
Figure 22:
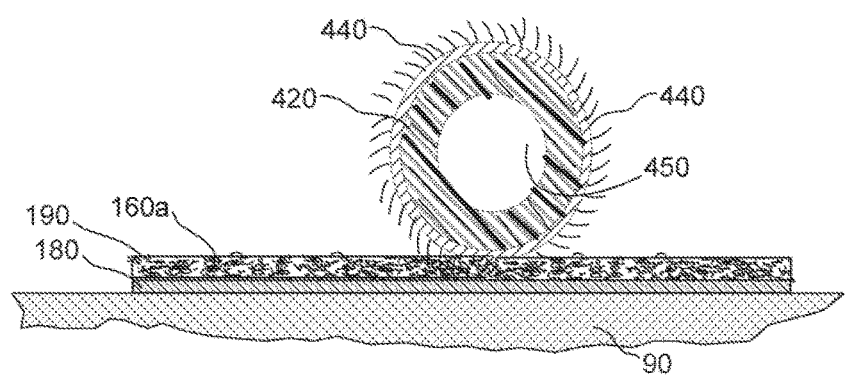
FIG. 22 is a cross-sectional view in elevation of the third alternative attachment member releasably securing the tubular surgical appliance to the surgical drape.

Referring to FIGS. 21 and 22, a third alternative attachment member 440 is adapted to releasably secure tubular member 420 to surgical field 30. In other words, third alternative attachment member 440 circumscribes tubular member 420 and defines a passageway 450 for receiving tubular member 420 therethrough. An outer circumference 444 having male "hooks" intimately engage the female "loops" of attachment member 160a that is adhesively attached to surgical field 30. Third alternative attachment member 440 may be included with any of the surgical kit embodiments described herein.

Illustrative Methods

An illustrative method associated with an exemplary embodiment for a surgical appliance kit and system will now be described.

Figure 23:
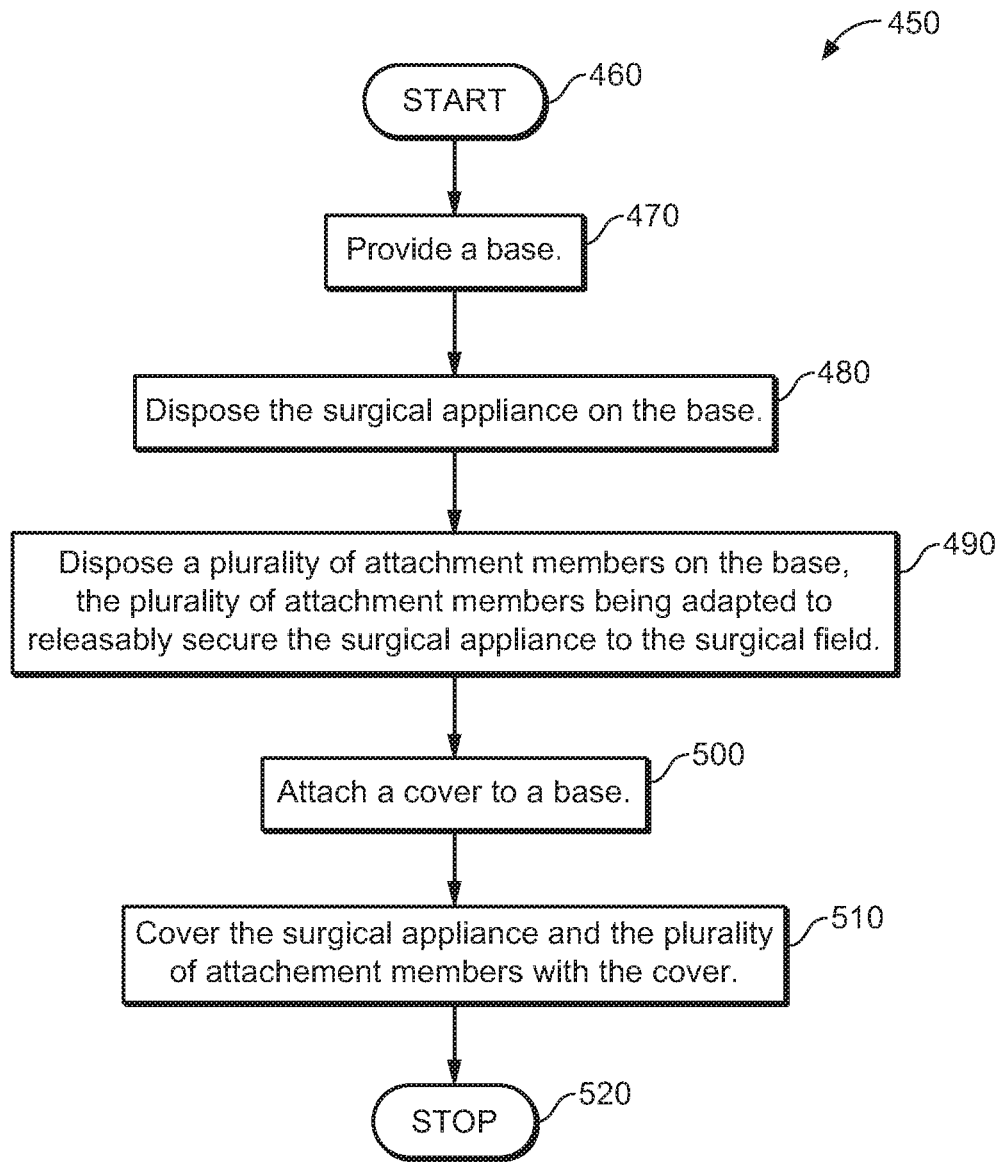
FIG. 23 is a flowchart showing an illustrative method of assembling the surgical appliance kit.

Referring to FIG. 23, an illustrative method 450 that is provided for assembling a surgical appliance kit starts at a block 460. At a block 470, a base is provided. At a block 480, a surgical appliance is disposed on the base. At a block 490, a plurality of attachment members is disposed on the base, the plurality of attachment members being adapted to releasably secure the surgical appliance to the surgical field. At a block 500, a cover is attached to the base. At a block 510, the surgical appliance and the plurality of attachment members are covered by the cover. The method stops at a block 520.

Based on the teachings herein, it may be appreciated that surgical appliance kits 10/220/230/240/250/320/330/340 may be used primarily with disposable surgical appliances. Disposable surgical appliances that drop to floor 110 cannot be conveniently resterilized due to there plastic components. Therefore, such disposable surgical appliances must be replaced with a new surgical appliance. In other words, if a disposable surgical appliance falls to floor 110, the disposable surgical appliance is permanently unusable and is, in this sense, lost forever. When this occurs, the disposable surgical appliance must be immediately replaced. However, replacing surgical appliances is expensive, takes time to replace the disposable appliance, results in a longer surgical procedure, and causes the patient to be under anesthesia longer, in addition to other undesirable consequences. Only metal nondisposable surgical appliances can be steam flashed sterilized for continuing the surgerical procedure. Although made of metal, if a nondisposable surgical appliance falls to floor 110, the nondisposable surgical appliance nonetheless may become damaged and possibly permanently unusable. However, even if the nondisposable surgical appliance were still usable, the nondisposable surgical appliance would still not be usable during the surgical procedure due to its contact with floor 110.

The preceding merely illustrates the principles of the invention. It will thus be appreciated that those skilled in the art will be able to devise various arrangements which, although not explicitly described or shown herein, embody the principles of the invention and are included within its spirit and scope. Furthermore, all examples and conditional language recited herein are principally intended expressly to be only for pedagogical purposes and to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention, as well as specific examples thereof, are intended to encompass both structural and functional equivalents thereof. Additionally, it is intended that such equivalents include both currently known equivalents and equivalents developed in the future, i.e., any elements developed that perform the same function, regardless of structure.

This description of the exemplary embodiments is intended to be read in connection with the figures of the accompanying drawing, which are to be considered part of the entire written description. In the description, relative terms such as "lower," "upper," "horizontal," "vertical," "above," "below," "up," "down," "top" and "bottom" as well as derivatives thereof (e.g., "horizontally," "downwardly," "upwardly," etc.) should be construed to refer to the orientation as then described or as shown in the drawing under discussion. These relative terms are for convenience of description and do not require that the apparatus be constructed or operated in a particular orientation. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise.

All patents, publications, scientific articles, web sites, and other documents and materials referenced or mentioned herein are indicative of the levels of skill of those skilled in the art to which the invention pertains, and each such referenced document and material is hereby incorporated by reference to the same extent as if it had been incorporated by reference in its entirety individually or set forth herein in its entirety. Applicants reserve the right to physically incorporate into this specification any and all materials and information from any such patents, publications, scientific articles, web sites, electronically available information, and other referenced materials or documents to the extent such incorporated materials and information are not inconsistent with the description herein.

The written description portion of this patent includes all claims. Furthermore, all claims, including all original claims as well as all claims from any and all priority documents, are hereby incorporated by reference in their entirety into the written description portion of the specification, and Applicants reserve the right to physically incorporate into the written description or any other portion of the application, any and all such claims. Thus, for example, under no circumstances may the patent be interpreted as allegedly not providing a written description for a claim on the assertion that the precise wording of the claim is not set forth in haec verba in written description portion of the patent.

The claims will be interpreted according to law. However, and notwithstanding the alleged or perceived ease or difficulty of interpreting any claim or portion thereof, under no circumstances may any adjustment or amendment of a claim or any portion thereof during prosecution of the application or applications leading to this patent be interpreted as having forfeited any right to any and all equivalents thereof that do not form a part of the prior art.

All of the features disclosed in this specification may be combined in any combination. Thus, unless expressly stated otherwise, each feature disclosed is only an example of a generic series of equivalent or similar features.

It is to be understood that while the invention has been described in conjunction with the detailed description thereof, the foregoing description is intended to illustrate and not limit the scope of the invention, which is defined by the scope of the appended claims. Thus, from the foregoing, it will be appreciated that, although specific embodiments of the invention have been described herein for the purpose of illustration, various modifications may be made without deviating from the spirit and scope of the invention. Other aspects, advantages, and modifications are within the scope of the following claims and the present invention is not limited except as by the appended claims.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. Thus, for example, in each instance herein, in embodiments or examples of the present invention, the terms "comprising", "including", "containing", etc. are to be read expansively and without limitation. The methods and processes illustratively described herein suitably may be practiced in differing orders of steps, and that they are not necessarily restricted to the orders of steps indicated herein or in the claims.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by various embodiments and/or preferred embodiments and optional features, any and all modifications and variations of the concepts herein disclosed that may be resorted to by those skilled in the art are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

It is also to be understood that as used herein and in the appended claims, the singular forms "a," "an," and "the" include plural reference unless the context clearly dictates otherwise, the term "X and/or Y" means "X" or "Y" or both "X" and "Y", and the letter "s" following a noun designates both the plural and singular forms of that noun. In addition, where features or aspects of the invention are described in terms of Markush groups, it is intended and those skilled in the art will recognize, that the invention embraces and is also thereby described in terms of any individual member or subgroup of members of the Markush group.

Other embodiments are within the following claims. The patent may not be interpreted to be limited to the specific examples or embodiments or methods specifically and/or expressly disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

Although the invention has been described in terms of exemplary embodiments, it is not limited thereto. Rather, the appended claims should be construed broadly, to include other variants and embodiments of the invention, which may be made by those skilled in the art without departing from the scope and range of equivalents of the invention.

Other modifications and implementations will occur to those skilled in the art without departing from the spirit and the scope of the invention as claimed. For example, a hook-configured attachment member may be adhesively attached to a side of surgical drape 90 opposite patient's 70 skin and a loop-configured attachment member may be attached to patient's 70 skin in alignment with the hook-configured attachment member. The hook-configured attachment member is then pressed into intimate engagement with the loop-configured attachment member, so that surgical drape 90 is connected to patient's 70 skin. The loop-configured attachment member is attached to patient's 70 skin by a suitable adhesive that allows the loop-configured attachment member to be removed from patient's skin only when required. In this manner, surgical drape 90, having surgical appliance releasably secured thereto, is prevented from slipping and falling to floor 110 and contaminating both surgical drape 90 and surgical appliance 20. Accordingly, the description hereinabove is not intended to limit the invention, except as indicated in the following claims.

Therefore, provided herein are a surgical appliance kit and system for releasably securing a surgical appliance to a surgical field and a method of assembling the surgical appliance kit.

What is claimed is:

1. A surgical appliance kit, comprising:
at least one multi-layered surgical drape laminate for use in a surgical field to facilitate enabling a surgical drape to cooperate with at least one surgical appliance for releasably securing the at least one surgical appliance to said surgical drape at about a specific location on the surgical drape, wherein the least one multi-layered surgical drape laminate further comprises; a flexible protective sheeting material layer having a distal side and a proximal side, an adhesive layer having a proximal side and a distal side such that the proximal side of the flexible protective sheeting material layer is located over the distal side of the adhesive layer, and a hook or loop configuration layer having a proximal side and a distal side such that the distal side of the hook or loop configuration is located adjacent to the proximal side of the adhesive layer, wherein the least one multi-layered surgical drape laminate is operatively connected to the surgical drape along the distal side of the adhesive layer after the flexible protective sheeting material layer has been peeled away;
at least one multi-layered surgical appliance laminate for use in the surgical field to facilitate enabling said at least one surgical appliance to cooperate with said surgical drape for releasably securing said surgical drape to said at least one surgical appliance at about a specific location on the surgical appliance, wherein the least one multi-layered surgical appliance laminate further comprises; a flexible protective sheeting material layer having a distal side and a proximal side, an adhesive layer having a proximal side and a distal side such that the proximal side of the flexible protective sheeting material layer is located over the distal side of the adhesive layer, and a hook or loop configuration layer having a proximal side and a distal side such that the distal side of the hook or loop configuration is located adjacent to the proximal side of the adhesive layer, wherein the least one multi-layered surgical appliance laminate is operatively connected to the surgical appliance along the distal side of the adhesive layer after the flexible protective sheeting material layer has been peeled away;
an indicator to provide a visual indication whether said at least one multi-layered surgical drape laminate and said at least one multi-layered surgical appliance laminate have been exposed to a pre-sterilization process and are suitable for use in the surgical field; and
a sealed pouch having peel away enabling means to enable separation between two surfaces for helping to enclose, retain, and retrieve when needed said at least one multi-layered surgical drape laminate, said at least one multi-layered surgical appliance laminate, and said indicator.

2. The surgical appliance kit of claim 1, further comprising:
confining means including another indicator to provide a visual indication whether said surgical drape and said at least one surgical appliance have been exposed to another pre-sterilization process and are suitable for use in a surgical procedure;
wherein said confining means helps to contain, enclose and hermetically seal said at least one multi-layered surgical drape laminate, said at least one multi-layered surgical appliance laminate, said indicator, said another indicator, and said pouch in close proximity to one another within said confining means for portable transportation to the surgical field for use in the surgical procedure; and
wherein said sealed pouch defines an interior volume for receiving therein said at least one multi-layered surgical drape laminate, said at least one multi-layered surgical appliance laminate, and said indicator.

3. The surgical appliance kit of claim 2, wherein said confining means has a sufficient interior volume to retain said at least one surgical appliance.

4. The surgical appliance kit of claim 3, wherein said confining means has a sufficient interior volume to retain at least another surgical appliance; and
wherein said another surgical appliance includes at least one multi-layered surgical appliance laminate removably secured thereto.

5. The surgical appliance kit of claim 3, wherein said confining means has a sufficient enough volume to retain at least another surgical appliance; and
wherein said another surgical appliance includes at least one multi-layered surgical appliance laminate permanently secured thereto.

6. The surgical appliance kit of claim 2, wherein said pouch is provided with a sealed access end portion to help seal and enclose said at least one multi-layered surgical drape laminate, said at least one multi-layered surgical appliance laminate, and said indicator within said pouch to provide protection from contamination; and
wherein said sealed access end portion includes said peel away enabling means for providing access to said interior volume to facilitate removal of said at least one multi-layered surgical drape laminate, said at least one multi-layered surgical appliance laminate, and said indicator from said pouch.

7. The surgical appliance kit of claim 6, wherein said peel away enabling means has a cutout defined by a pair of opposing bendable pull tabs, said pair of opposing bendable pull tabs extending outwardly from said sealed access end portion a sufficient distance to facilitate tight finger engagement therewith for tab pulling purposes to open said sealed access end portion.

8. The surgical appliance kit of claim 2, wherein said confining means has a sufficient interior volume to contain and sealingly enclose said surgical drape.

9. The surgical appliance kit of claim 8, wherein said confining means has a sufficient interior volume to contain and sealingly enclose at least another surgical drape where said another surgical drape includes at least one multi-layered surgical drape laminate permanently secured thereto.

10. The surgical appliance kit of claim 2, wherein said confining means is a sealed tray.

11. The surgical appliance kit of claim 2, wherein said pouch includes an integrally formed transparent window portion for viewing a presence of said at least one multi-layered surgical drape laminate, said at least one multi-layered surgical appliance laminate, and said indicator within the interior volume defined by said pouch.

12. The surgical appliance kit of claim 2, wherein said confining means is constructed with a puncture-resistant material for helping to protect said at least one multi-layered surgical drape laminate, said at least one multi-layered surgical appliance laminate, said indicator, said another indicator, and said pouch from damage while said pouch is disposed on said confining means.

13. The surgical appliance kit of claim 2, wherein said confining means is further comprised of:
a plurality of individual recesses for substantially retaining said at least one multi-layered surgical drape laminate, said at least one multi-layered surgical appliance laminate, said surgical drape, said at least one surgical appliance and said indicator in substantially immobile positions relative to one another.

14. The surgical appliance kit of claim 1, wherein said at least one surgical appliance is selected from the group consisting essentially of:
a catheter surgical appliance, an electro-surgical cauterization surgical appliance, a scalpel surgical appliance, a bipolar radiofrequency surgical appliance, a suction surgical appliance, a biopsy forceps surgical appliance, a bandage and plaster shears surgical appliance, an orthopedic chisel surgical appliance, a lung retractor surgical appliance, a laryngeal forceps surgical appliance, a tongue depressor surgical appliance and combinations thereof.

15. The surgical appliance kit of claim 2, further comprising:
a date strip connected to an exterior surface of said confining means.

16. The surgical appliance kit of claim 2, further comprising:
a date strip connected to an interior surface of said confining means.

17. The surgical appliance kit of claim 1, wherein said at least one surgical appliance is a tubular member.

18. The surgical appliance kit of claim 1, wherein said at least one surgical appliance is deployable in said surgical field.

19. The surgical appliance kit of claim 1, wherein said surgical drape is deployable in said surgical field.

20. The surgical appliance kit of claim 1, wherein said at least one multi-layered surgical drape laminate and said at least one multi-layered surgical appliance laminate each include a plurality of hook-and-loop fasteners.

21. A surgical appliance kit, comprising:
a plurality of multi-layered surgical drape laminates for use in a surgical field to facilitate enabling at least one surgical drape to cooperate with at least one surgical appliance for releasably securing the at least one surgical appliance to the at least one surgical drape at about a specific location on the at least one surgical drape, wherein the at least one multi-layered surgical drape laminate further comprises; a flexible protective sheeting material layer having a distal side and a proximal side, an adhesive layer having a proximal side and a distal side such that the proximal side of the flexible protective sheeting material layer is located over the distal side of the adhesive layer, and a hook or loop configuration layer having a proximal side and a distal side such that the distal side of the hook or loop configuration is located adjacent to the proximal side of the adhesive layer, wherein at least one of the plurality of multi-layered surgical drape laminates is operatively connected to the surgical drape along the distal side of the adhesive layer after the flexible protective sheeting material layer has been peeled away;

a plurality of multi-layered surgical appliance laminates for use in the surgical field to facilitate enabling at least one surgical drape to cooperate with at least one surgical appliance for releasably securing the at least one surgical appliance to the at least one surgical drape at about a specific location on the at least one surgical drape, wherein the plurality of multi-layered surgical appliance laminates further comprise; a flexible protective sheeting material layer having a distal side and a proximal side, an adhesive layer having a proximal side and a distal side such that the proximal side of the flexible protective sheeting material layer is located over the distal side of the adhesive layer, and a hook or loop configuration layer having a proximal side and a distal side such that the distal side of the hook or loop configuration is located adjacent to the proximal side of the adhesive layer, wherein at least one of the plurality of multi-layered surgical appliance laminates is operatively connected to the surgical appliance along the distal side of the adhesive layer after the flexible protective sheeting material layer has been peeled away;

an indicator to provide a visual indication whether said plurality of multi-layered surgical drape laminates and said plurality of multi-layered surgical appliance laminates have been exposed to a pre-sterilization process and are suitable for use in the surgical field;

a sealed, pouch having peel away enabling means to enable separation between two surfaces for helping to enclose, retain, and retrieve when needed said plurality of multi-layered surgical drape laminates, said plurality of multi-layered surgical appliance laminates, and said indicator in close proximity to one another for their portable transportation to the surgical field for use in a surgical procedure;

wherein said pouch defines an interior volume therein for receiving said plurality of multi-layered surgical drape laminates, said plurality of multi-layered surgical appliance laminates, and said indicator; and wherein said pouch has a sealed access end portion to sealingly enclose said plurality of multi-layered surgical drape laminates, said plurality of multi-layered surgical appliance laminates, and said indicator for protecting said plurality of multi-layered surgical drape laminates, said plurality of multi-layered surgical appliance laminates, and said indicator from contamination.

22. The surgical appliance kit of claim 21, further comprising:

a confining means for sealingly enclosing said plurality of multi-layered surgical drape laminates, said multi-layered surgical appliance laminates, said indicator, said another indicator, and said pouch in close proximity to one another to for portable transportation to the surgical field for use in a surgical procedure;

another indicator located on said confining means to provide a visual indication whether said surgical drape and said at least one surgical appliance have been exposed to a pre-sterilization process and are suitable for use in the surgical field; and wherein said peel away enabling means forms part of said sealed access end portion and includes a cutout defined by a pair of opposing flaps, said pair of opposing flaps facilitating the unsealing and opening of the sealed access end portion of said pouch to provide access to said plurality of multi-layered surgical drape laminates, said plurality of multi-layered surgical appliance laminates, and said indicator.

23. The surgical appliance kit of claim 22, wherein said confining means has a sufficient enough volume to retain at least one surgical appliance.

24. The surgical appliance kit of claim 23, wherein said confining means has a sufficient enough volume to retain at least another surgical appliance; and wherein said another surgical appliance includes at least one multi-layered surgical appliance laminate of said plurality of multi-layered surgical appliance laminates removably secured thereto.

25. The surgical appliance kit of claim 23, wherein said confining means has a sufficient enough interior volume to retain at least another surgical appliance said another surgical appliance includes at least one multi-layered surgical appliance laminate of said plurality of multi-layered surgical appliance laminates permanently secured thereto.

26. The surgical appliance kit of claim 22, wherein said confining means has a sufficient interior volume to retain a surgical drape.

27. The surgical appliance kit of claim 26, wherein said confining means has a sufficient enough volume to retain at least another surgical drape wherein said another surgical drape includes at least one multi-layered surgical drape laminate of said plurality of multi-layered surgical drape laminates permanently secured thereto.

28. The surgical appliance kit of claim 22, wherein said confining means is a sealed tray wherein said plurality of multi-layered surgical drape laminates, said another indicator, said plurality of multi-layered surgical appliance laminates, and said pouch are disposed thereon.

29. The surgical appliance kit of claim 22, wherein said confining means comprises:

a puncture-resistant material protecting said plurality of multi-layered surgical drape laminates, said plurality of multi-layered surgical appliance laminates, said indicator, said another indicator, and said pouch from damage while said pouch is disposed on said confining means.

30. The surgical appliance kit of claim 22, further comprising:

a date strip connected to an exterior surface of said confining means.

31. The surgical appliance kit of claim 22, further comprising:

a date strip connected to an interior surface of said confining means.

32. The surgical appliance kit of claim 22, wherein said confining means is further comprised of:

a plurality of individual recesses for substantially retaining said plurality of multi-layered surgical drape laminates, said plurality of multi-layered surgical appliance laminates, said surgical drape, said at least one surgical appliance, and said indicator.

33. The surgical appliance kit of claim 21, wherein said pouch includes an integrally formed transparent window portion for viewing a presence of said plurality of multi-layered surgical drape laminates, said plurality of multi-layered surgical appliance laminates, and said indicator in the interior volume defined by said pouch.

34. The surgical appliance kit of claim 21, wherein said at least one surgical appliance is selected from the group consisting essentially of:
- a catheter surgical appliance, an electro-surgical cauterization surgical appliance, a scalpel surgical appliance, a bipolar radiofrequency surgical appliance, a suction surgical appliance, a biopsy forceps surgical appliance, a bandage and plaster shears surgical appliance, an orthopedic chisel surgical appliance, a lung retractor surgical appliance, a laryngeal forceps surgical appliance, a tongue depressor surgical appliance and combinations thereof.

35. The surgical appliance kit of claim 21, wherein said at least one surgical appliance is a tubular member.

36. The surgical appliance kit of claim 21, wherein said at least one surgical appliance is deployable in said surgical field.

37. The surgical appliance kit of claim 21, wherein said surgical drape is deployable in said surgical field.

38. The surgical appliance kit of claim 21, wherein said plurality of multi-layered surgical drape laminates and said plurality of multi-layered surgical appliance laminates comprise a plurality of hook-and-loop fasteners.

* * * * *